(12) United States Patent
Gardner et al.

(10) Patent No.: US 12,245,369 B2
(45) Date of Patent: Mar. 4, 2025

(54) METHODS AND SYSTEMS FOR FABRICATING 3D MULTIELECTRODE ARRAYS WITH 3D PRINTED ELECTRODES

(71) Applicant: University of Oregon, Eugene, OR (US)

(72) Inventors: Timothy Gardner, Eugene, OR (US); Kara Zappitelli, Oakland, CA (US); Morgan Brown, Eugene, OR (US)

(73) Assignee: University of Oregon, Eugene, OR (US)

( * ) Notice: Subject to any disclaimer, the term of this patent is extended or adjusted under 35 U.S.C. 154(b) by 287 days.

(21) Appl. No.: 17/738,817

(22) Filed: May 6, 2022

(65) Prior Publication Data

US 2022/0361323 A1    Nov. 10, 2022

Related U.S. Application Data

(60) Provisional application No. 63/185,859, filed on May 7, 2021.

(51) Int. Cl.
| | |
|---|---|
| *H05K 1/02* | (2006.01) |
| *A61N 1/05* | (2006.01) |
| *B29C 64/124* | (2017.01) |
| *B29L 31/34* | (2006.01) |
| *B33Y 10/00* | (2015.01) |

(Continued)

(52) U.S. Cl.
CPC ......... *H05K 1/0296* (2013.01); *B29C 64/124* (2017.08); *B33Y 10/00* (2014.12); *B33Y 40/20* (2020.01); *B33Y 80/00* (2014.12); *H05K 1/0346* (2013.01); *H05K 1/0393* (2013.01); *H05K 1/09* (2013.01); *H05K 3/06* (2013.01); *H05K 3/10* (2013.01); *A61N 1/0526* (2013.01);

(Continued)

(58) Field of Classification Search
None
See application file for complete search history.

(56) References Cited

U.S. PATENT DOCUMENTS

2021/0033559 A1    2/2021    Panat et al.

FOREIGN PATENT DOCUMENTS

| | | | |
|---|---|---|---|
| CN | 109875557 A | * | 6/2019 |
| JP | H09274845 A | * | 10/1997 |

OTHER PUBLICATIONS

CN-109875557-A (2024).*

(Continued)

*Primary Examiner* — Hoa C Nguyen
*Assistant Examiner* — John B Freal
(74) *Attorney, Agent, or Firm* — Klarquist Sparkman, LLP

(57) ABSTRACT

Methods and systems for fabricating 3D electronic devices, such as multielectrode arrays, including metalized, 3D printed structures using integrated 3D printing and photolithography techniques are disclosed. As one embodiment, a multielectrode array comprises a flexible substrate, a plurality of photopatterned electrical traces spaced apart and insulated from one another on the substrate, and a plurality of 3D printed electrodes. Each 3D printed electrode comprises a photopolymer coated in metal and has a 3D structure that extends outward from the substrate, and each 3D printed electrode is electrically connected to a corresponding electrical trace of the plurality of photopatterned electrical traces.

20 Claims, 22 Drawing Sheets

(51) Int. Cl.
- *B33Y 40/20* (2020.01)
- *B33Y 80/00* (2015.01)
- *H05K 1/03* (2006.01)
- *H05K 1/09* (2006.01)
- *H05K 3/06* (2006.01)
- *H05K 3/10* (2006.01)

(52) U.S. Cl.
CPC ............. *B29L 2031/3406* (2013.01); *H05K 2201/0154* (2013.01)

(56) References Cited

OTHER PUBLICATIONS

JP H09274845 A (2024).*
Al-Abaddi et al., "Fabrication of 3D nano/microelectrodes via two-photon-polymerization," *Microelectronic Engineering*, vol. 98, pp. 378-381 (Jul. 2012).
Bonabi et al., "Metallization of Organically Modified Ceramics for Microfluidic Electrochemical Assays," *Micromachines*, vol. 10, 12 pp. (Sep. 2019).
Bonabi, "Microfabrication of Organically Modified Ceramics for Bio-MEMS," Academic Dissertation, University of Helsinki Finland, 85 pp. (Jan. 2020).
Kleber et al., "A Novel 3D Microelectrode Array for Extracellular Signal Recording of Acute Brain Slices," *9th Int'l Meeting on Substrate Integrated Microelectrode Arrays*, pp. 280-281 (Jul. 2014).
Multi Channel Systems MCS GmbH, "3D Microelectrode Arrays for 3D cell culture, tissue slices and cell clusters," Product Flyer, 2 pp. (Jun. 2018).
Multi Channel Systems MCS GmbH, "Microelectrode Arrays," downloaded from https://www.multichannelsystems.com/products/microelectrode-arrays, 1 p. (downloaded on Mar. 9, 2021).
NeuroOne Medical Technologies Corporation, "Evo Cortical Electrode Portfolio," downloaded from https://n1mtc.com/evo-cortical, 2 pp. (downloaded on Mar. 9, 2021).
Pearre et al., "Fast micron-scale 3D printing with a resonant-scanning two-photon microscope," *Additive Manufacturing*, vol. 30, 10 pp. (Oct. 2019).

* cited by examiner

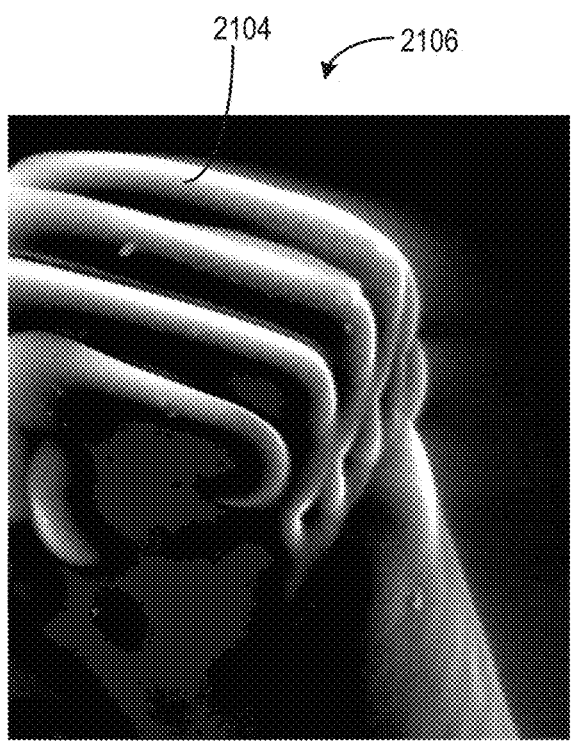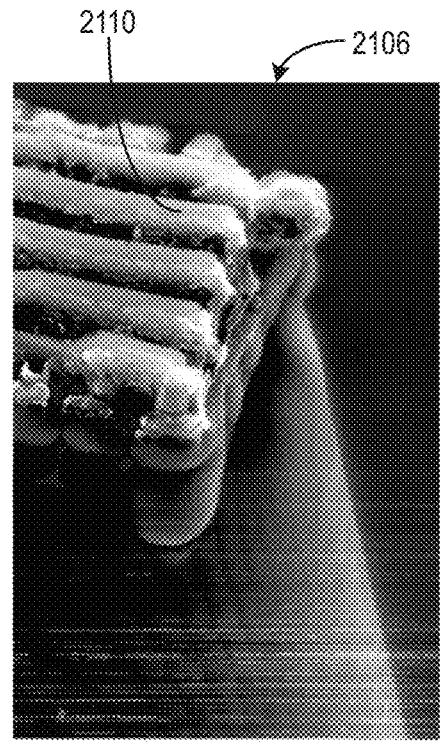
FIG. 25  FIG. 26
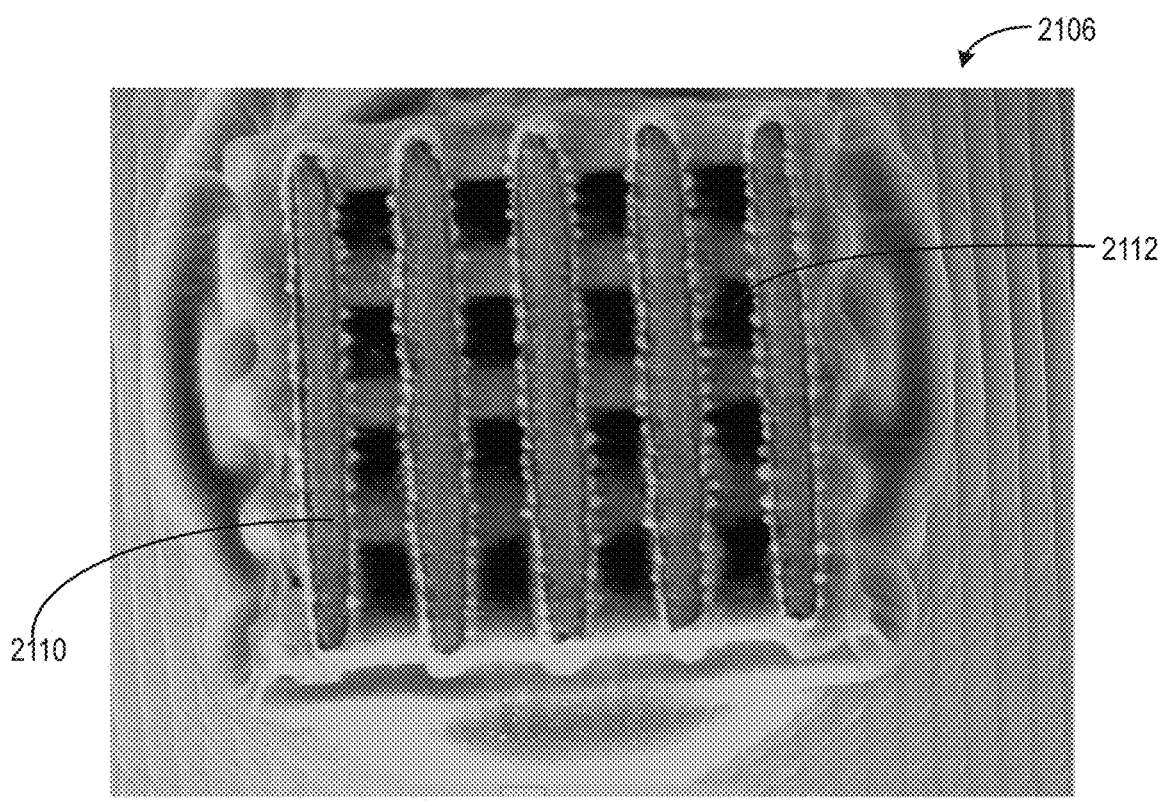
FIG. 27

METHODS AND SYSTEMS FOR FABRICATING 3D MULTIELECTRODE ARRAYS WITH 3D PRINTED ELECTRODES

CROSS-REFERENCE TO RELATED APPLICATION

This application claims the benefit of U.S. Provisional Patent Application No. 63/185,859, filed May 7, 2021, which is incorporated by reference herein in its entirety.

ACKNOWLEDGEMENT OF GOVERNMENT SUPPORT

This invention was made with government support under Grant Nos. R01NS104925 and R01NS118424 awarded by the NIH. The government has certain rights in the invention.

FIELD

The present disclosure relates generally to methods and systems for fabricating 3D electronic devices, such as multielectrode arrays, including metalized, 3D printed structures using integrated 3D printing and photolithography techniques.

BACKGROUND

Thin film multielectrode arrays comprising a flexible substrate and a plurality of electrodes configured for electrical stimulation and/or recording can be used in a variety of applications. For example, such multielectrode arrays can be used for in vitro cell culture applications and in vivo applications, such as in neural applications in the body (recording and stimulation applications, for example). In some embodiments, thin film multielectrode arrays can be produced with microfabrication techniques, such as photolithography. However, utilizing photolithography to pattern electrodes and other electronic components on a thin film or other flexible substrates (e.g., a wafer) can result in planar devices with relatively planar or flat electrodes. When used for tissue applications (in vitro or in vivo), such planar multielectrode arrays may sit on the surface of the tissue, and thus, can be limited in their application, stimulation and/or recording potential, and duration of use.

SUMMARY

Disclosed herein are multielectrode arrays comprising a plurality of 3D electrodes on a substrate. Each 3D electrode comprises a photopolymer forming a 3D structure that extends outward from the substrate and that is coated in metal. Further, metal coating each 3D electrode can be electrically connected to a corresponding electrical trace of a plurality of photopatterned electrical traces on the substrate. In some embodiments, the 3D structure of each 3D electrode can be raised relative to the substrate (extend outward) such that the 3D structure has a relatively high aspect ratio and/or surface area to footprint ratio (e.g., an aspect ratio of at least 10:1). Disclosed also herein are methods of fabricating such 3D multielectrode arrays using a combination of photolithography and 3D printing techniques.

In one representative embodiment, a multielectrode array comprises a substrate, a plurality of photopatterned electrical traces spaced apart and insulated from one another on the substrate, and a plurality of 3D electrodes. Each 3D electrode comprises a photopolymer coated in metal and having a 3D structure that extends outward from the substrate and has an aspect ratio of at least 10:1, where each 3D electrode is electrically connected to a corresponding electrical trace of the plurality of photopatterned electrical traces.

In some embodiments, for at least a portion of the plurality of 3D electrodes, the 3D structure has a conical shape with a base disposed at the substrate and a tip that is disposed away from the substrate and is narrower than the base.

In some embodiments, for at least a portion of the plurality of 3D electrodes, the 3D structure comprises a base disposed on the substrate, and a shaft portion that extends from the base and narrows to a tip portion of the 3D structure.

In some embodiments, the tip portion comprises a sharp tip that tapers from a sloped base extending from an end of the shaft portion.

In some embodiments, the multielectrode array is coated with an insulating layer, and the tip portion of each 3D electrode comprises exposed metal that is not covered by the insulating layer.

In some embodiments, a spacing between adjacent 3D electrodes of the plurality of 3D electrodes on the substrate is in a range of 80-100 μm.

In some embodiments, the 3D structure of each 3D electrode is a 3D printed structure.

In some embodiments, each 3D electrode has a height in a range of 300-400 μm.

In some embodiments, the substrate is a thin film substrate comprising polyimide.

In another representative embodiment, a method of forming a 3D multielectrode array comprises defining a plurality of electrical contacts, a plurality of electrical traces, and a plurality of print pads on a substrate of the 3D multielectrode array using photopatterning and applying a sacrificial metal layer comprising a metal over the substrate. The method further comprises etching the sacrificial metal layer to expose the plurality of electrical contacts and the plurality of pint pads, each print pad contacting a corresponding electrical trace of the plurality of electrical traces which is connected to a corresponding electrical contact of the plurality of electrical contacts. The method further comprises 3D printing a plurality of 3D structures onto the exposed plurality of print pads, each print pad receiving one 3D structure of the plurality of 3D structures, wherein each 3D structure extends outward from the substrate and has a height and applying a layer of metal over the exposed plurality of electrical contacts, the plurality of 3D structures, and a remaining portion of the sacrificial metal layer. The method further comprises lifting off the remaining portion of the sacrificial metal layer to reveal the 3D multielectrode array which comprises a plurality of metallized 3D structures, each metallized 3D structure electrically connected to the corresponding electrical contact through the corresponding electrical trace.

In some embodiments, applying the sacrificial metal layer occurs before the defining, and the defining further includes applying a positive photoresist onto a surface of the sacrificial metal layer and uncovering the plurality of electrical contacts, the plurality of electrical traces, and the plurality of print pads by exposing a portion of the positive photoresist covering the plurality of electrical contacts, the plurality of electrical traces, and the plurality of print pads to UV light (e.g., via a laser or mercury lamp).

In some embodiments, the applying the sacrificial metal layer occurs after the defining, and the defining further includes photopatterning the plurality of electrical contacts and the plurality of electrical traces onto the substrate using an initial metal layer, applying a photo-patternable insulator over the plurality of electrical contacts and the plurality of electrical traces, and opening windows through the insulator to expose the plurality of electrical contacts and define the plurality of print pads on the substrate.

In some embodiments, the method further comprises coating the 3D multielectrode array with a layer of an insulating material and removing the insulating material from tips of each metallized 3D structure using a laser.

In some embodiments, each 3D structure has an aspect ratio in a range of 10:1 to 40:1

In some embodiments, the metal of the sacrificial metal layer comprises chromium, and wherein the plurality of 3D structures comprises a photopolymer.

In some embodiments, the substrate comprises a thin film, flexible polymer.

In another representative embodiment, a multielectrode array comprises a thin film, polyimide substrate including a plurality of photopatterned electrical traces spaced apart from one another on the substrate; and a plurality of 3D printed electrodes, each 3D printed electrode comprising a 3D printed structure disposed on a portion of the substrate that is connected to a corresponding electrical trace of the plurality of photopatterned electrical traces, each 3D printed electrode metallized such that it is electrically connected to the corresponding electrical trace. Each 3D printed electrode has an aspect ratio of at least 10:1 and each metallized 3D printed electrode is coated in an insulating layer, except for a conductive, exposed tip of the metallized 3D printed electrode In some embodiments, the insulating layer further covers the plurality of photopatterned electrical traces and the substrate.

In some embodiments, the 3D printed structure of each 3D printed electrode comprises a photopolymer, and the photopolymer is coated with metal to form the 3D printed electrode.

In some embodiments, for at least a portion of the plurality of 3D printed electrodes, the 3D printed structure comprises a base disposed on the substrate and spike structure that extends from the base and narrows to a peak of the 3D printed structure.

In another representative embodiment, a multielectrode array comprises a substrate; a plurality of photopatterned electrical traces spaced apart and insulated from one another on the substrate; and a plurality of 3D electrodes, each 3D electrode comprising a photopolymer coated in metal and having a porous 3D structure that extends outward from the substrate and includes a plurality of pores, wherein each 3D electrode is electrically connected to a corresponding electrical trace of the plurality of photopatterned electrical traces.

In another representative embodiment, a multielectrode array comprises a thin film substrate including a plurality of photopatterned electrical traces spaced apart from one another on the substrate; and a plurality of 3D printed electrodes, each 3D printed electrode comprising a 3D printed structure disposed on a portion of the substrate that is connected to a corresponding electrical trace of the plurality of photopatterned electrical traces, each 3D printed electrode metallized such that it is electrically connected to the corresponding electrical trace. Each 3D printed electrode comprises a plurality of pores extending into an interior of the 3D printed structure and has an aspect ratio greater than one.

In another representative embodiment, a method for forming a three-dimensional (3D) multielectrode array comprises: photopatterning a plurality of electrical contacts and a plurality of electrical traces onto a substrate of the 3D multielectrode array; 3D printing a plurality of 3D structures, each 3D structure comprising a photopolymer and a plurality of pores, onto exposed portions of the substrate, wherein each exposed portion of the substrate is connected to a corresponding electrical trace of the plurality of electrical traces; and for each 3D structure, selectively metallizing the 3D structure on the exposed portion of the substrate using photolithography to form the 3D multielectrode array and such that the metallized 3D structure is covered in metal, has open pores extending into an interior of the metallized 3D structure, and is in electrical contact with the corresponding electrical trace and a corresponding electrical contact of the plurality of electrical contacts.

In another representative embodiment, a method of forming a 3D multielectrode array, comprises: photopatterning a plurality of electrical contacts and a plurality of electrical traces onto a substrate of the 3D multielectrode array; applying a sacrificial metal layer comprising a metal over the substrate and the plurality of electrical contacts and the plurality of electrical traces; etching the sacrificial metal layer to expose the plurality of electrical contacts and a plurality of pint pads on a surface of the substrate, each print pad contacting a corresponding electrical trace of the plurality of electrical traces which is connected to a corresponding electrical contact of the plurality of electrical contacts; 3D printing a plurality of 3D structures onto the plurality of print pads, each print pad receiving one 3D structure of the plurality of 3D structures, wherein each 3D structure extends outward from the substrate and has a height; applying a layer of metal to the exposed plurality of electrical contacts, the plurality of 3D structures, and a remaining portion of the sacrificial metal layer; and lifting off the remaining portion of the sacrificial metal layer to reveal the 3D multielectrode array which comprises a plurality of metallized 3D structures, each metallized 3D structure electrical connected to the corresponding electrical contact through the corresponding electrical trace.

In another representative embodiment, a 3D electronic device comprises: a substrate with an electrical contact; and a metallized, 3D printed structure disposed on a surface of the substrate and in electrical contact with the electrical contact, the 3D printed structure comprising a photopolymer and having a surface area to footprint ratio greater than 2:1 and including a plurality of pores that are spaced apart from one another on an outer surface of the 3D printed structure and each extend into an interior of the 3D printed structure.

In another representative embodiment, a multielectrode array comprises a flexible substrate, a plurality of photopatterned electrical traces spaced apart and insulated from one another on the substrate, and a plurality of 3D printed electrodes. Each 3D printed electrode comprises a photopolymer coated in metal and has a 3D structure that extends outward from the substrate. Each 3D printed electrode is electrically connected to a corresponding electrical trace of the plurality of photopatterned electrical traces.

The foregoing and other objects, features, and advantages of the disclosed technology will become more apparent from the following detailed description, which proceeds with reference to the accompanying figures.

BRIEF DESCRIPTION OF THE DRAWINGS

FIG. 25 is an exemplary microscopic image of the tip of one 3D printed electrode of the device of FIG. 24 before removing the insulating material from the tip.

FIG. 26 is an exemplary microscopic image of a perspective view of the tip of one 3D printed electrode of the device of FIG. 24 after removing the insulating material from the tip to expose a conductive metal surface of the tip.

FIG. 27 is an exemplary microscopic image of a top view of the tip of one 3D printed electrode of the device of FIG. 24 after removing the insulating material from the tip to expose a conductive metal surface of the tip.

DETAILED DESCRIPTION

Thin film multielectrode arrays can be used in a wide variety of applications, including (but not limited to) in vitro cell culture, neural stimulation and/or recording in vivo, computer chip testing, and the like. These arrays can be produced using photolithography, which results in relatively compact and/or small-scale devices. By utilizing various photolithography techniques to pattern parts onto a thin film substrate, more flexible electrode arrays can be produced. Smaller electrode arrays (e.g., on a micron scale) may be desirable for multielectrode arrays that are implanted within the body (such as the brain).

However, traditional thin film lithography may only be able to produce relatively flat (e.g., planar) multielectrode arrays. In some instances, lithography techniques may be capable of producing slopes or rounded forms, but such shapes can require a large number of fabrication steps, thereby increasing a cost and fabrication time of such a device. Thus, producing multielectrode arrays comprising electrodes with a structure that is raised from a base of the substrate of the array (e.g., has a relatively high aspect ratio or surface area to footprint ratio), and having a specified shape based on a specified application, may not be possible with such fabrication techniques.

Figure 1A:
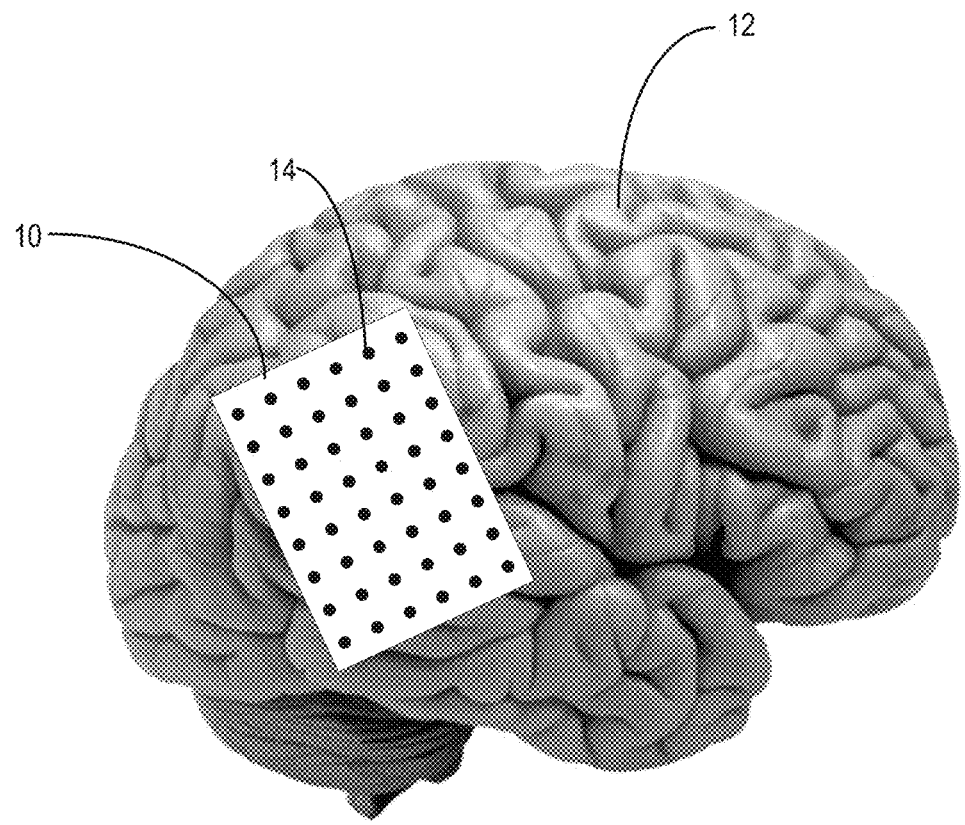
FIG. 1A shows an exemplary planar electrode array that comprises a plurality of separate, planar electrodes and that is configured to sit on a surface of the brain, according to an embodiment.
Figure 1B:
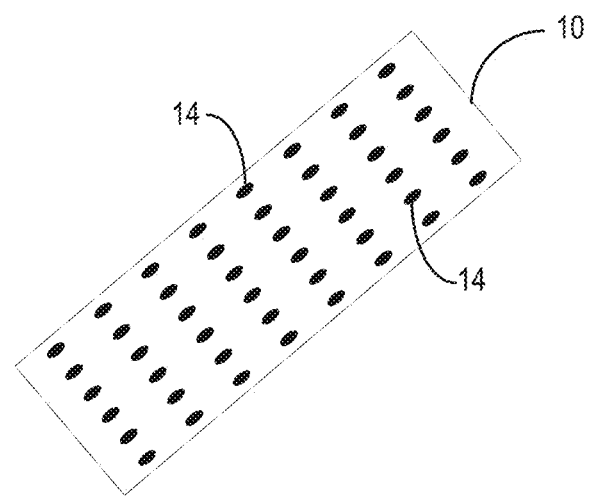
FIG. 1B is a perspective view of the planar electrode array of FIG. 1A.

As an example, when used for tissue applications, such as implantation in the body (e.g., brain, heart, spinal cord, or the like), multielectrode arrays comprising relatively planar electrodes that sit on or against the surface of the tissue can have reduced effectiveness and applicability. For example, FIGS. 1A and 1B show an exemplary planar multielectrode array 10 (perspective view shown in FIG. 1B) that is configured to sit on a surface of the brain 12 (FIG. 1A). The planar multielectrode array 10 can comprise a plurality of separate, planar electrodes 14 which have a relatively low surface area to footprint ratio or aspect ratio (e.g., are not raised substantially or at all from a base surface of the array). For example, the electrodes 14 do not have a shape and height (e.g., in a direction out of the page) that allows them to penetrate into the surface of the tissue (e.g., of the brain 12 in FIG. 1A). As a result, the multielectrode array 10 is configured to sit on the surface of the tissue (e.g., brain tissue, as shown in FIG. 1A).

The more planar, 2D nature of the planar multielectrode array 10 (and similar multielectrode arrays) can cause scar tissue ingrowth to occur following implantation. This limits the electrode array's ability to form long-term electrical connections with the brain tissue. For example, scar tissue may form against the planar multielectrode array 10 implanted in the brain, thereby reducing its stimulation and/or recording capabilities and reducing its effectiveness for longer-term stimulation or recording applications (e.g., for deep brain therapy in patients with Parkinson's or other chronic neurological disorders).

Additionally, thin film, flat electrodes and electrode arrays, such as the planar multielectrode array 10, may have a lower electrode surface area and surface area to footprint ratio, and thus, deliver less charge or electrical potential. Thus, such arrays may utilize a larger number of electrodes and/or electrodes with increased width or diameter to increase the amount of charge they can deliver. However, this increases the overall footprint of the device (e.g., as shown in FIG. 1A, with the array 10 covering a large portion of the brain 12), thereby increasing a time to fabricate such a device and the scar tissue that may form as a result of implanting the device.

Further still, as mentioned above, since the electrodes of the planar multielectrode array 10 are planar, they cannot penetrate the tissue (e.g., brain tissue). As a result, the applications that they can be used for is limited (e.g., they cannot be used for deep brain stimulation) and they may not adhere to or anchor well to the tissue in which they are implanted. This can further limit their longevity for implantation in the body. Thus, thin film, planar multielectrode arrays, such as the planar multielectrode array 10 of FIGS. 1A and 1B, may not be able to stimulate the brain (or other anatomical tissue) effectively and for a longer period of time (e.g., months or years).

The present disclosure pertains to multielectrode arrays comprising raised electrode structures that are composed of a photopolymer that is coated in metal (thereby creating electrodes) and methods for manufacturing such arrays. In some embodiments, the raised electrode structures forming the electrodes of the multielectrode array can be 3D printed to have a height that extends outward from a base (e.g., substrate) of the multielectrode array. For example, electrode structures having a certain height can result in electrodes with a relatively high surface area to footprint ratio (and/or aspect ratio, such as an aspect ratio of at least 10:1). Thus, the multielectrode arrays described herein may be referred to as 3D multielectrode arrays.

Additionally, in some embodiments, the 3D multielectrode arrays described herein can be configured as thin film multielectrode arrays that comprise a flexible, thin film substrate.

In some embodiments, 3D multielectrode arrays that are configured to penetrate tissue, anchor to the surface of the tissue in which they are implanted, and/or enable tissue ingrowth can be produced by integrating micron-scale additive manufacturing (e.g., 3D printing) with photolithography techniques. These 3D multielectrode arrays can penetrate the tissue in which they are implanted and provide the potential for surface anchoring and/or cell ingrowth, unlike more traditional 2D multielectrode arrays produced using photolithography alone, due to their 3D geometry. For example, such 3D multielectrode arrays can comprise 3D structures with more than a single planar surface for electrical communication.

Further, the 3D printed electrodes of the 3D (thin film) multielectrode arrays described herein can be highly customizable for specific applications (e.g., shape, size, and the like), and thus, these arrays can be highly adaptable for a variety of applications (e.g., implantation in different types of tissue, recording and/or stimulating applications, cell culture applications, and for stimulating different parts of a tissue with one device).

As used herein, "photolithography" (or "lithography") or "photolithography techniques" can refer to methods of microfabrication that are used to pattern parts onto a thin film or bulk substrate (or wafer). Photolithography (or photopatterning) can refer to methods that utilize light to transfer a geometric pattern from a photomask to a photosensitive (light-sensitive) chemical photoresist in the desired pattern upon the material under the photoresist.

As used herein, a 3D electronic device, component, or electrode may refer to a device that has a raised, 3D structure (e.g., more than a single layer) with an aspect ratio and/or surface area to footprint ratio that is greater than 1 (e.g., 1:1) and larger than more traditional electrical components formed via photolithography (or thin film) fabrication alone (e.g., without 3D printing 3D structures onto a substrate). For example, though photolithography alone may result in electrical structures comprising one or more thin layers of metal, 3D printing 3D structures can comprise numerous layers of a material forming a 3D structure with a high surface area to footprint ratio that can then be metalized.

Further, as used herein, a "surface area to footprint ratio" of a 3D structure (or 3D printed structure) can refer to a ratio between a surface area of the 3D structure and a footprint of the 3D structure. The "footprint" of the 3D structure can refer to the 2D surface area that the 3D structure occupies on a substrate or base material (e.g., the substrate of the electrode array). In this way, by having a more 3D structure that extends away from the substrate (e.g., in the z direction), a larger surface area to footprint ratio is created. Said another way, 3D structures can provide a larger surface area for electrical communication while occupying a smaller 2D space on a substrate.

Additionally, as used herein, an "aspect ratio" of a 3D structure (or 3D printed structure) can be defined as a ratio of the height (along the z-axis) of the 3D structure to a width or diameter of the 3D structure (along an x or y-axis), where a base or substrate from which the 3D structure extends is defined in the x-y plane.

Figure 2A:
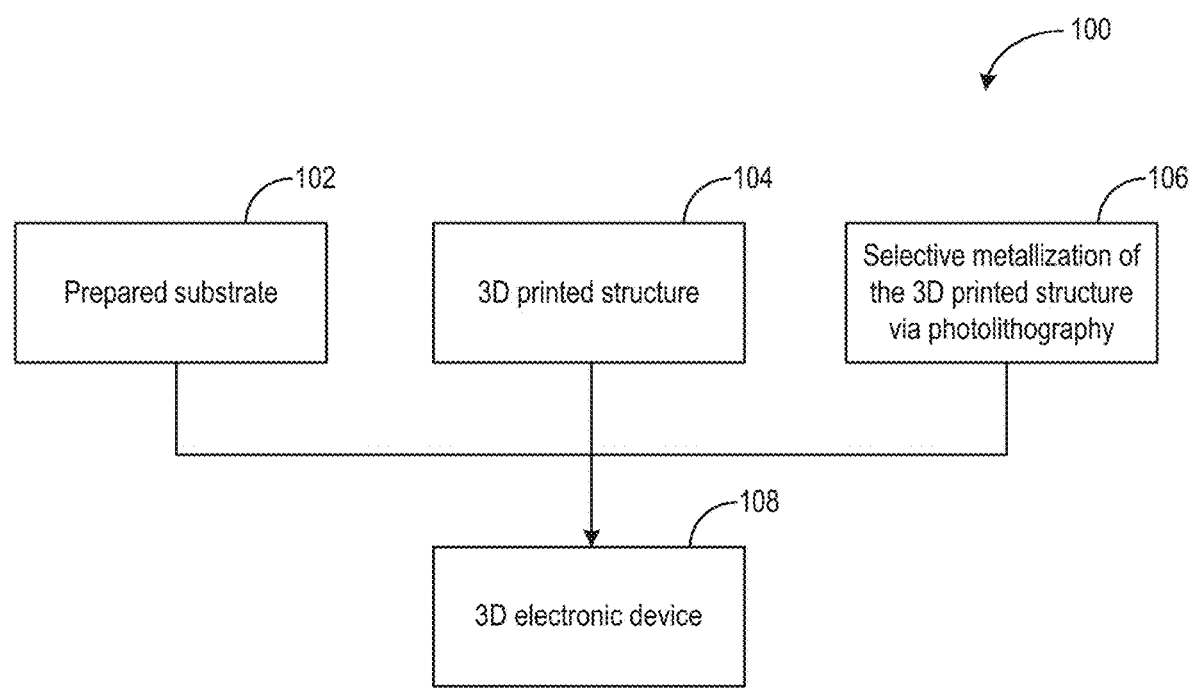
FIG. 2A is a schematic of an exemplary process for integrating 3D printing and photolithography fabrication techniques to create 3D electronic components and/or devices.

FIG. 2A is a schematic of an exemplary process 100 for integrating 3D printing and photolithography fabrication techniques to create 3D electronic components and/or devices that include one or more electrodes or electrical components with a higher surface area to footprint ratio or higher aspect ratio (e.g., as compared to more two-dimensional electrical components manufactured by photolithography or other electrical fabrication techniques alone). In some embodiments, the fabricated 3D electronic device or component can be on the scale of microns (e.g., micron scale). For example, the process 100 can be used to produce thin film multielectrode arrays comprising 3D printed electrodes that comprise a photopolymer. Further, in some embodiments, the 3D printed electrodes can have a plurality of pores, thereby further increasing their surface area (e.g., for electrostimulation and/or for tissue ingrowth, as described further below). Additionally or alternatively, the 3D printed electrodes can have a conical or spike-like shape with an aspect ratio of at least 10:1.

As shown in FIG. 2A, the process 100 can include combining a prepared substrate 102 with one or more 3D printed structures (e.g., 3D structures that comprise a photopolymer) 104 and selective metallization of the 3D structure(s) via photolithography, at 106, to form a 3D electronic device 108, such as a multielectrode array comprising a plurality of isolated electrodes. The 3D electronic device 108 can be configured to transmit and/or receive electrical signals over a relatively large electrical contact surface area (e.g., electrochemical surface area) and/or penetrate an object in which it is implanted (e.g., tissue for an implantable multielectrode array). For example, as discussed further herein, each electrical contact or electrode of the 3D electronic device 108 can have more than a single planar surface (e.g., as produced via traditional photolithography alone, without 3D printed structures) or a higher surface area to footprint ratio or aspect ratio for receiving and/or transmitting electrical signals or charge. Thus, when the 3D electronic device is an electrode, for example, the 3D electrode can deliver a larger amount of electrical potential per surface area that it occupies on the substrate (as compared to a more 2D or flat electrode). Further, such a 3D electrode or array of multiple 3D electrodes can be configured to penetrate tissue (such as the dura of the brain). Such devices can also enhance anchoring of the 3D electronic device 108 and reduce immune response and scar tissue formation.

The prepared substrate 102 can comprise a thin film or flexible material, such as a silicon-based material (e.g., silicon dioxide or silica) or polyimide. In some embodiments, the prepared substrate 102 can comprise glass, silicon, or a polymer (e.g., polyimide).

In some embodiments, the prepared substrate 102 can include one or more metal traces (e.g., electrical contacts) that are insulated from one another and one or more windows that are opened to receive the 3D printed structure 104 and connected to respective metal traces of the one or more metal traces.

As discussed further below with reference to FIGS. 3 and 4, the 3D printed structure 104 can be formed using a 3D printing technique. In some embodiments, the 3D printing technique can include raster-scanning direct laser writing lithography. As an example, the 3D printed structure can be printed using a raster-scanning direct laser writing (rDLW) printer (FIG. 4A, which can also be referred to as a direct laser writing two-photon 3D printer). The rDLW printer is capable of printing micron scale polymer structures at increased speeds (e.g., 8000 mm/s, which can be ten to thousands of times faster than other high-speed based DLW printers), as discussed further below with reference to FIG. 4A.

While more traditional and commercially available additive manufacturing (e.g., 3D printing) systems can readily produce 3D structures, these 3D structures are either larger in scale (e.g., greater than the micron scale) or very small scale (e.g., nano scale). Thus, such 3D printing systems may not integrate well with micron scale electronics fabrication (e.g., microfabrication), such as photolithography.

The increased scanning speed of the rDLW printer allows for printing of the 3D printed structure 104 onto the prepared substrate 102 with relatively high resolution on the micron scale. As a result, multielectrode arrays having a high density of 3D electrodes can be achieved. For example, a spacing or pitch between adjacent 3D electrodes of the 3D multielectrode array can be approximately 90 μm (however, a spacing down to about 30 μm and up to about 9 mm can also be produced, as described further below).

The selective metallization of the 3D printed structure via lithography, at 106, can include performing photolithography techniques to metalize the 3D printed structure 104, thereby electrically connecting the metalized 3D printed structure with the corresponding metal traces on the substrate 102, while maintaining non-metalized (insulated) space on the substrate, around the metalized 3D printed structure. As a result, electronic devices, electrodes, and/or circuits can be produced with electrically insulated or separated electrodes or electrical components.

In some embodiments, the specific combination of 3D printing with the rDLW printer and metallization of the 3D printed structure via photolithography (e.g., microfabrication technique) allows the 3D electronic device 108 to be fabricated in an efficient manner.

Further, as described in more detail below with reference to FIGS. 8A-11C, 23, 30A, and 30B, by combining 3D printing with the photolithography techniques, 3D electronic devices with electrodes or electronic components having specific external shapes or geometries and/or internal geometrical features (e.g., pores, channels, or the like), can be created. As discussed further herein, this allows these 3D electronic devices to be used in a variety of applications and easily tailored for a selected application, including in vivo applications.

Figure 2B:
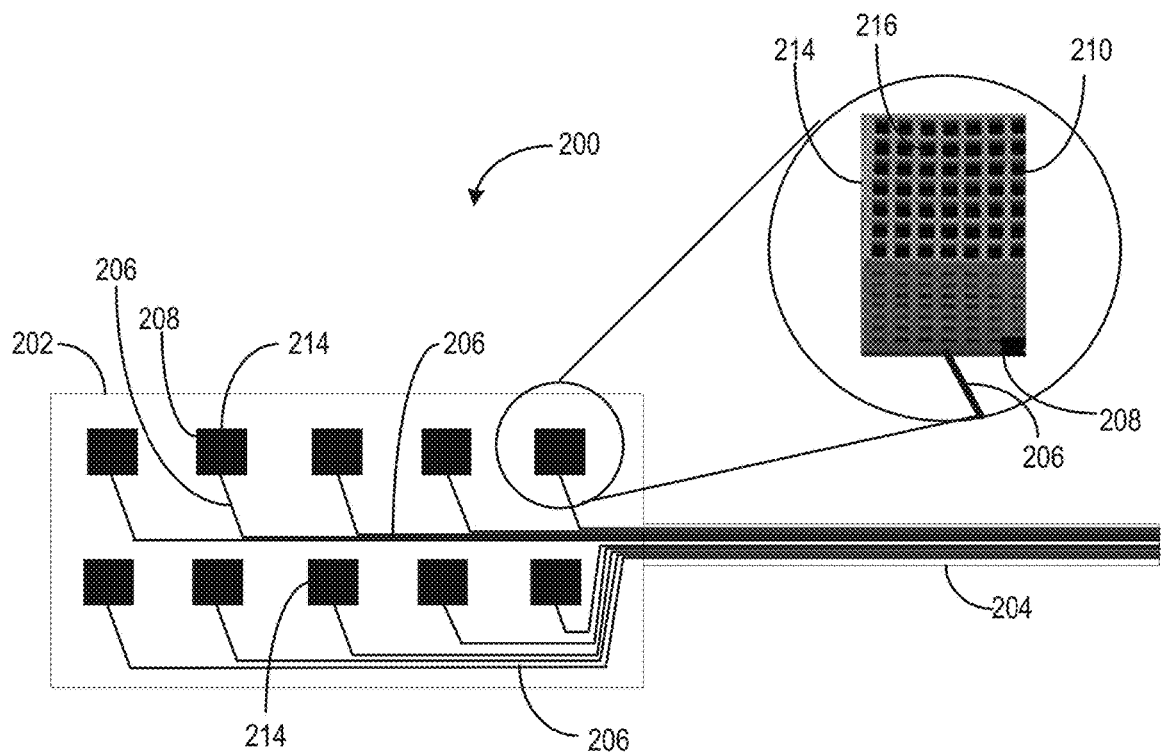
FIG. 2B is a schematic of an exemplary 3D electrode array comprising a plurality of 3D electrodes formed on a substrate.

An exemplary embodiment of a 3D electronic device that can be fabricated using the process depicted in FIG. 2A is shown in FIG. 2B. Specifically, FIG. 2B is a schematic of an exemplary 3D multielectrode array (array of electrodes) 200 comprising a plurality of 3D printed electrodes 214 (e.g., that can comprise a photopolymer) formed on a base or substrate 202 with photopatterned electrical connections (also referred to as traces) 206.

For example, as shown in FIG. 2B, the 3D multielectrode array 200 can comprise the substrate 202 and a tail (or connector) 204 extending away from the substrate 202. Each of a plurality of electrical connections 206 (e.g., traces or strips of metal) can extend along the tail 204 and across the substrate 202 to connect with a corresponding electrical contact or pad 208 and 3D electrode 214 of the plurality of 3D electrodes. For example, the substrate 202 can include a plurality of spaced apart electrical contacts or pads 208 (e.g., electrode pads), each of which is directly and electrically connected to a different one of the plurality of electrical connections 206 or is configured to receive a metalized electrode 214, thereby electrically connecting it to a different one of the plurality of electrical connections 206.

Figure 12A:
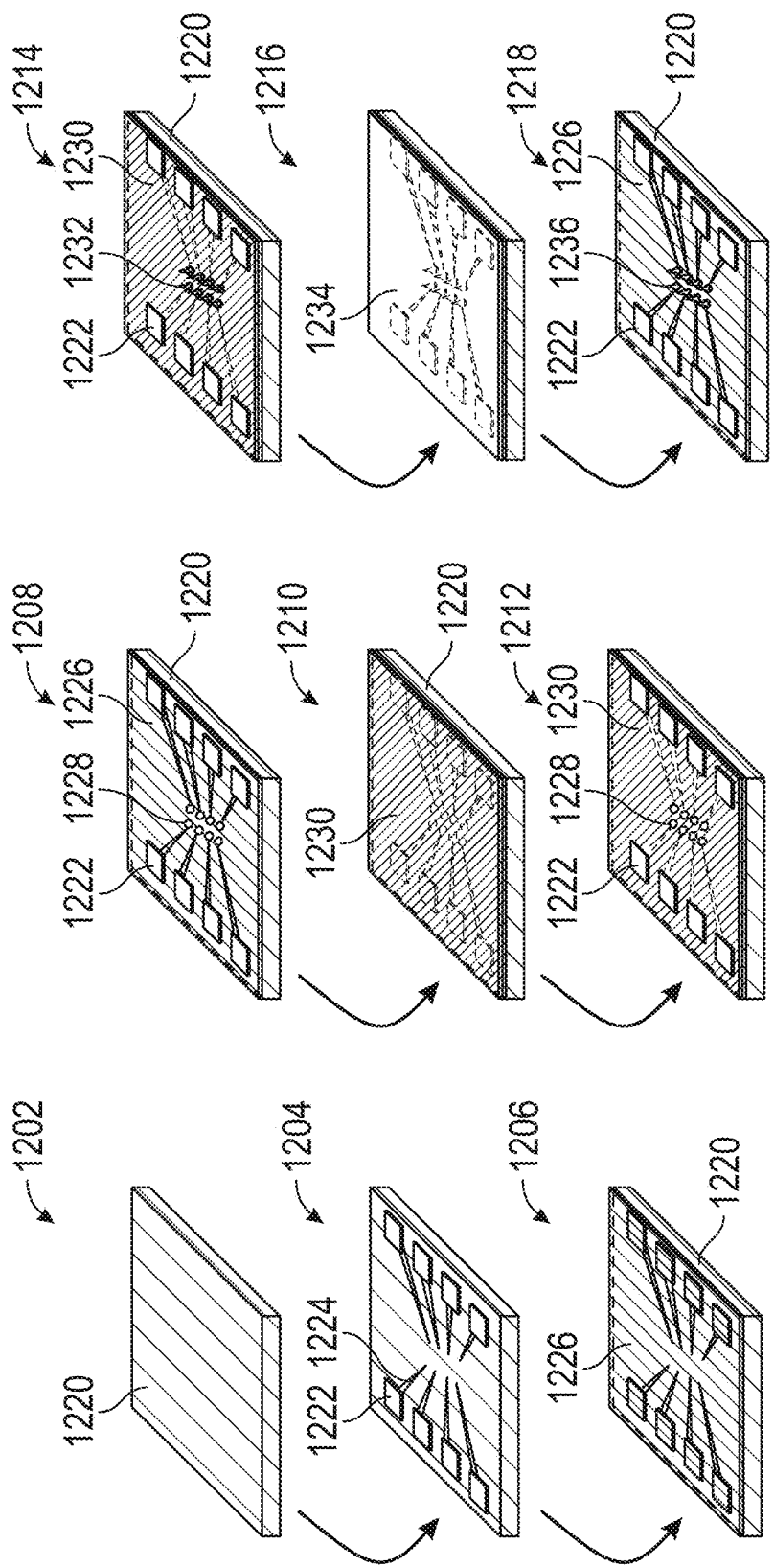
FIG. 12A is a schematic showing an exemplary process for fabricating a fully metallized and insulated 3D multi-electrode array with metallized 3D printed structures that are electrically connected to predefined electrical traces and contacts of the device.
Figure 12B:
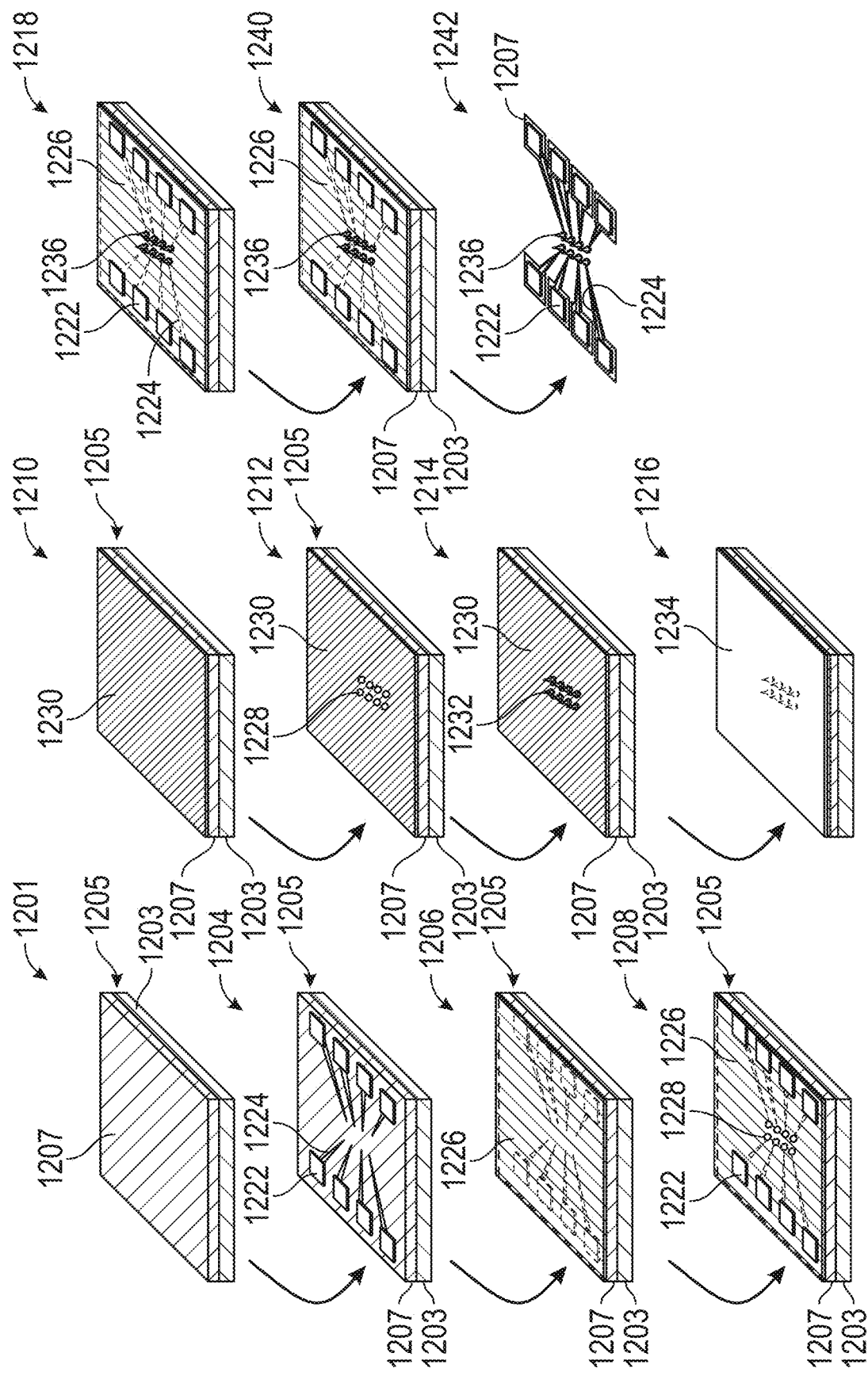
FIG. 12B is another schematic showing an exemplary process for fabricating a fully metallized and insulated 3D multielectrode array with metallized 3D printed structures that are electrically connected to predefined electrical traces and contacts of the device and are printed onto a flexible substrate.

In alternate embodiments, the multielectrode array 200 may not comprise the tail 204 and instead, the substrate can include a plurality of exposed electrical contacts that are each electrically connected to a corresponding one of the electrical connections 206 and a metallized electrode 214 (e.g., as shown in FIGS. 12A and 12B, described further below).

Each electrode 214 can be connected to a corresponding electrical contact or pad 208. For example, each electrode 214 can comprise a metalized, 3D printed structure 210 disposed adjacent and electrically connected to the corresponding electrical contact or pad 208.

In some embodiments, the 3D printed structure 210 can include one or more pores 216. The one or more pores 216 can extend from an outer surface of the 3D printed structure 210 into an interior of (and in some embodiments, through) the 3D printed structure 210. In other embodiments, the 3D structure can include one or more channels, depressions, extensions, or other geometric features. In still other embodiments, the 3D printed structure 210 can be a relatively solid body (without pores or channels) with a conical, shank, or spike-like 3D structure having an aspect ratio of at least 10:1.

Different embodiments of 3D printed structures that can form the electrodes or other electrical components of an electronic device, such as the 3D multielectrode array 200, are shown in FIGS. 8A-11C, 13-15, 17-19, 23, 24, 30A, and 30B as described further below.

Figure 3:
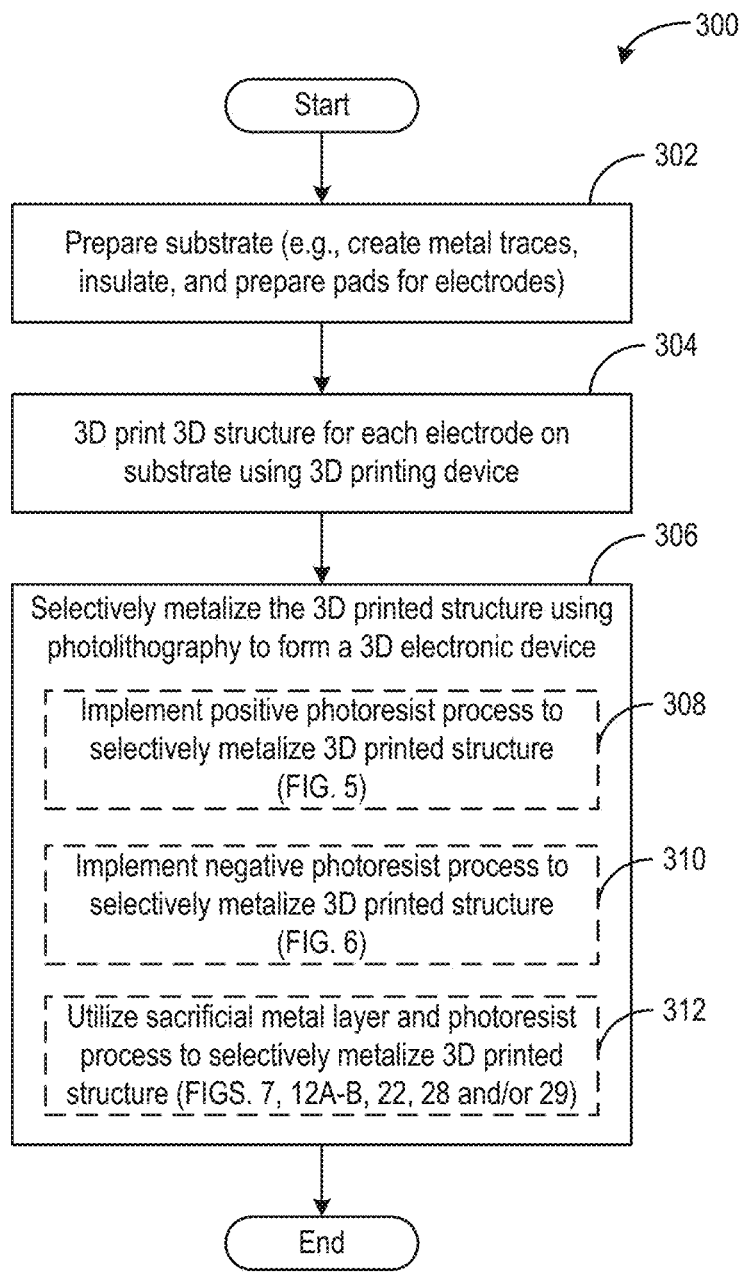
FIG. 3 is a flow chart of a method for manufacturing a 3D electronic device, such as a 3D multielectrode array, with integrated 3D printing and photolithography methods.

Turning to FIG. 3, a method 300 for manufacturing (e.g., fabricating) a 3D electronic component or device, such as the 3D multielectrode array 200 of FIG. 2 or another 3D electronic device, as described herein, is shown.

Method 300 begins at 302 and includes preparing a substrate of the 3D electronic device. In some embodiments, the substrate can comprise a flexible material or a silicon-based material. In some embodiments, the substrate can comprise glass, silicon, or a polymer. In some embodiments the substrate can comprise a thin film polymer (or polymeric material, such as polyimide).

In some examples, preparing the substrate at 302 can include adding a flexible substrate material (e.g., polyimide) over a more rigid substrate (e.g., silicon). For example, as shown at 1201 in FIG. 12B, polyimide can be spun onto the surface of a silicon wafer 1203, thereby forming a substrate 1205 that comprises the silicon wafer 1203 (or other base substrate) that is covered by a polyimide layer 1207 (or another thin film material layer) (FIG. 12B).

Preparing the substrate at 302 can include patterning (photopatterning) electrical contacts and traces (interconnects) (or windows for the electrical contacts and traces) onto a substrate and creating one or more windows, pads, or spaces that are each connected to a corresponding electrical trace and that are open and configured to receive a 3D printed structure.

For example, as shown at 1204 in FIGS. 12A and 12B, in some embodiments, electrical contacts and/or traces (e.g., comprising metal) can be patterned onto a substrate 1220 (clean substrate shown at 1202 in FIG. 12A) or substrate 1205 (FIG. 12B) using photolithography methods and then a photo-patternable insulator can be spun or deposited on top of the electrical contacts 1222 and/or traces 1224, thereby forming an insulating layer 1226 (as shown at 1206 in FIGS. 12A and 12B). In some embodiments, the insulator can be SU-8 negative photoresist or another type of photo-patternable insulating material.

In some embodiments, the method at 302 can further include using standard photolithography techniques to open one or more windows or spaces 1228 through the top insulating layer 1226 down to the substrate 1220 (FIG. 12A) or polyimide layer 1207 (FIG. 12B) and to expose the electrical contacts 1222 (as shown at 1208 in FIGS. 12A and 12B). The windows 1228 are configured to receive the 3D printed structure, and thus can also be referred to as print pads, as described further below.

Figure 5:
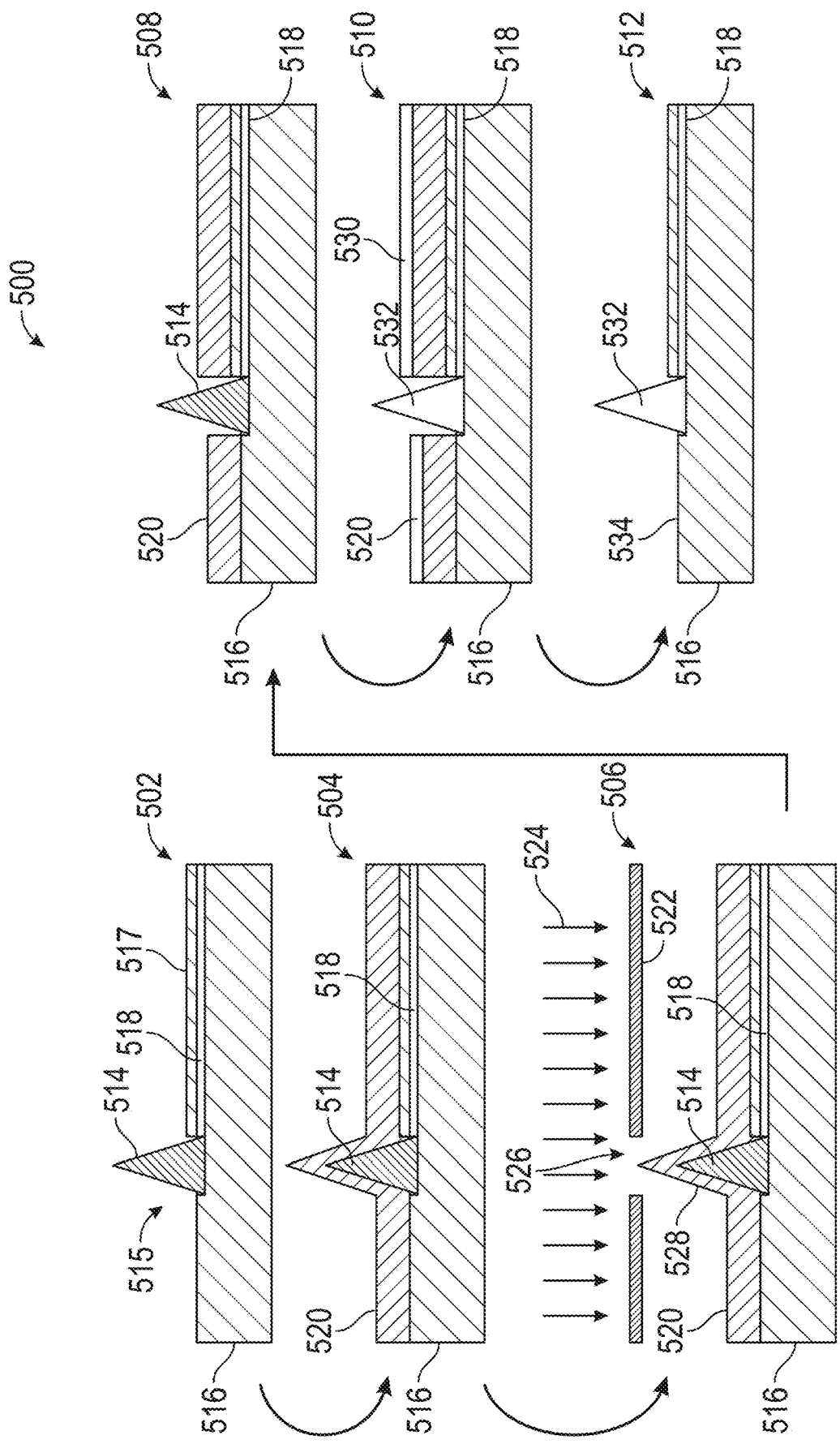
FIG. 5 is a schematic showing an exemplary process for implementing a positive photoresist lithography process to selectively metallize a 3D printed structure.

As another example, as shown in FIG. 5 (and similarly, FIG. 6), in some embodiments, the substrate (e.g., substrate 516 in FIG. 5) can include a top insulating layer 517 and preparing the substrate at 302 can include using standard photolithography techniques to open one or more windows or spaces 515 through the top insulating layer 517 down to a portion of the substrate that is adjacent to the predefined electrical contacts 518 (see FIGS. 5 and 6 and related description below).

In some embodiments, preparing the substrate at 302 can include or further include sputtering a sacrificial metal layer 1230 comprising a metal (a sacrificial metal layer) onto the surface of the substrate or the insulating layer 1226 on top of the substrate 1220 or substrate 1205 (as shown at 1210 in FIGS. 12A and 12B). In some embodiments, the sacrificial metal layer 1230 can comprise aluminum or chromium. The sacrificial metal layer 1230 can then be etched to reopen the electrical contacts 1222 and windows 1228 (as shown at 1212 in FIG. 12A) or etched to reopen just the windows 1228 (as shown at 1212 in FIG. 12B).

In some embodiments, as shown in the exemplary methods of FIGS. 7, 22, 28, and 29 (as described in further detail below), this etching process can include spinning a photoresist (e.g., positive photoresist) onto the surface of the sacrificial metal layer and an outline of specified electrical contacts or metal traces can be defined using a laser writer (e.g., a 405 nm laser writer). The laser-exposed photoresist can then be removed when exposed to a developer (e.g., developer solution). An acidic metal etchant can then be applied (e.g., via submersion or washing), thereby removing a portion of the sacrificial metal layer that is uncovered by the photoresist. In this way, the photoresist can serve as an etch mask for the sacrificial metal layer in an acidic metal etchant. Thus, this process results in etching down to the surface of the substrate in a specified location on the substrate. The above-described method at 302 that can include utilizing the sacrificial metal layer is described in further detail below with reference to FIGS. 7, 22, 28, and 29.

Once the substrate has been prepared such that it is ready to receive one or more 3D printed structures, method 300 proceeds to 304 which can include 3D printing a 3D structure onto one or more specified portions of the substrate using a 3D printing device. For example, the one or more specified portions of the substrate can include the portions of the substrate that were opened up to expose the underlying substrate or (in other embodiments) electrical contacts.

In some embodiments, the 3D printing technique used to print the 3D structure at 304 can include raster-scanning direct laser writing (rDLW), which can also be referred to as two photon lithography. DLW printing technology is based on two photon polymerization (2PP), where a tightly focused laser is pulsed at femtosecond speeds while being scanned through a polymerizable liquid. In some embodiments, the 3D printing the 3D structure can include using a rDLW printer, such as the rDLW printer shown in FIG. 4A, to print a predetermined 3D structure, layer-by-layer, onto the specified portions of the substrate. The predetermined 3D structure can be defined by a computer model of the 3D structure (e.g., 3D computer aided design (CAD) model) which is input into a computer or processor included in or in electronic communication with the rDLW printer.

In some embodiments, the polymerizable liquid, and thus the resulting 3D printed 3D structure, can comprise a polymer (e.g., a photopolymer).

Figure 4A:
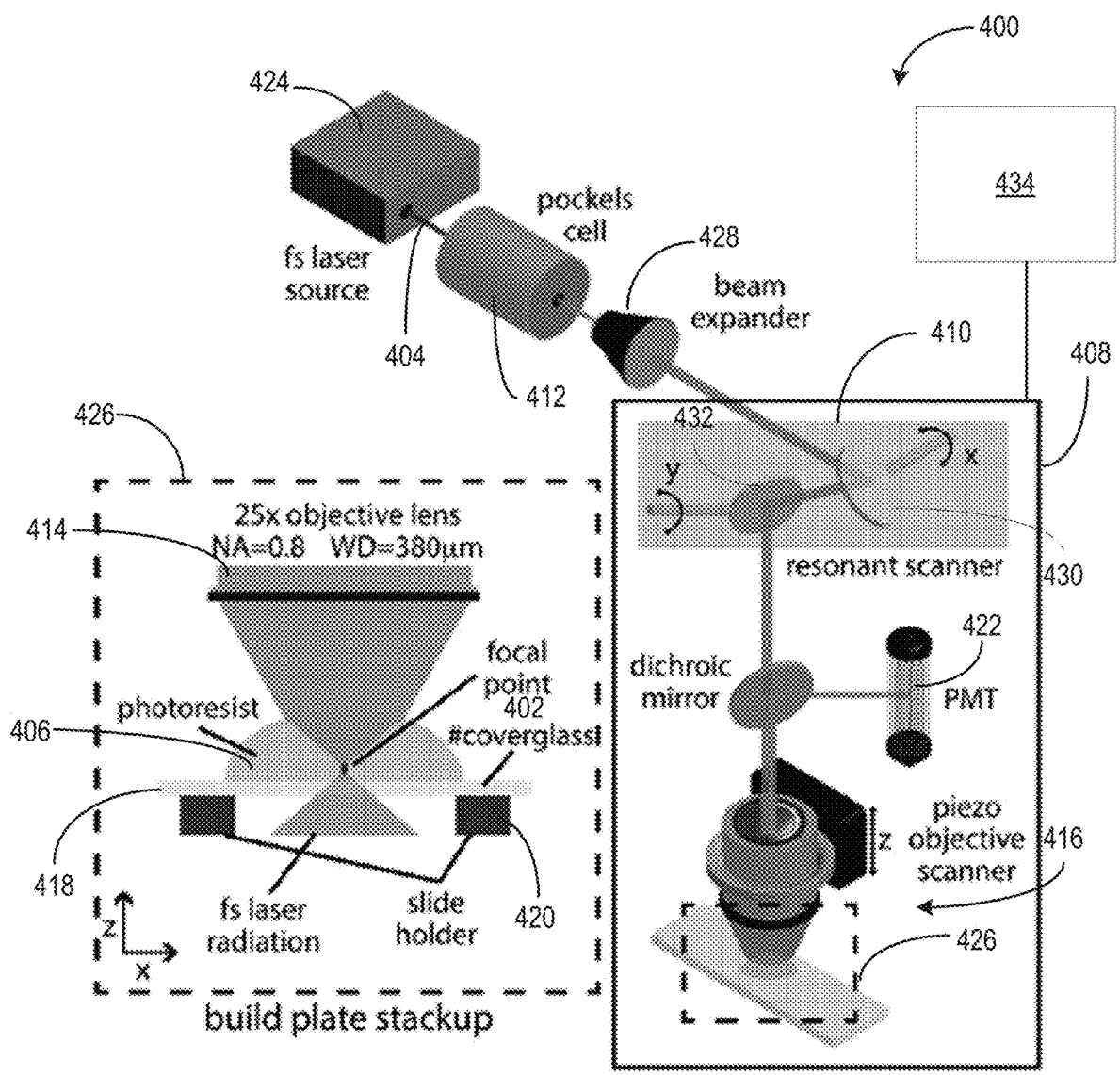
FIG. 4A is a schematic of an exemplary raster-scanning direct laser writing (rDLW) printer.

Turning to FIG. 4A, an exemplary rDLW printer 400 that can be used to print the 3D structure at 304 is shown. The rDLW printer 400 can fabricate 3D objects by raster-scanning a focal point 402 of a laser beam (e.g., femtosecond laser beam) 404 through a build volume or build envelope 406 (which, in some embodiments can comprise a volume of photoresist or other polymer), thereby defining the object structure line by line.

In some embodiments, as shown in FIG. 4A, the rDLW printer 400 can comprise a standard two-photon microscope 408 with a resonant raster scanner 410 and a high-speed/high-extinction-ratio laser power modulator 412.

Figure 4B:
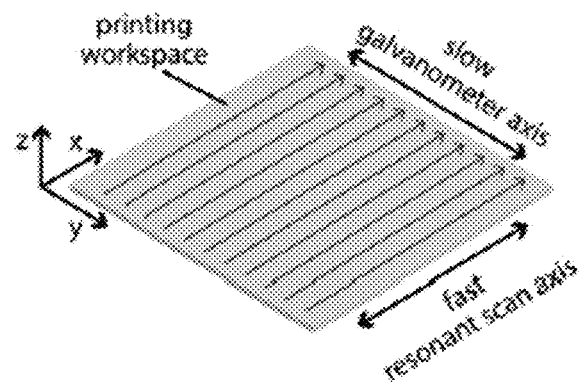
FIG. 4B is a schematic showing directions and dimensions in a build envelope of the rDLW printer of FIG. 4A.

As used herein and as shown in FIG. 4B, Cartesian coordinates refer to directions and dimensions in the build envelope. The X and Y axes or directions are the perpendicular axes spanning a single focal plane of the orthogonal Z direction. The zoom setting of the microscope 408 can determine the size of this X-Y plane, which can be referred to as the "workspace". As shown in FIG. 4B, X denotes the direction of the faster sweeps of the high-speed (e.g., about 8 kHz) resonant raster scanner 410, and Y identifies the slower galvanometer-controlled row index.

The resonant raster scanner 410, which in some embodiments can be a resonant and galvanometer scan module, can control the X-Y focal point 402 of the laser beam 404 within the build envelope 406. For example, the resonant raster scanner 410 can comprise a resonant mirror 430 which controls the focal point 402 along the X-axis and a galvanometer mirror 432 which controls the focal point 402 point along the Y-axis.

As shown in the detail view of a build stack plate 426 of the rDLW printer 400, an immersion objective lens 414, which in some embodiments can include a refraction compensation ring, can be used for both printing and imaging.

The rDLW can further comprise a piezo-scanner 416 which can enable fast, precise Z-axis positioning of the objective lens 414 (and hence the focal plane) during printing. In some embodiments, the substrate of the 3D electronic device is positioned on a build plate 418 which is supported at its edges by one or more holding mechanisms 420. In other embodiments, the substrate of the 3D electronic device can replace the build plate and be connected to the one or more holding mechanisms 420.

In some embodiments, the rDLW printer 400 can include an imaging device 422 which can be configured to image the workspace and printed objects, such as a photomultiplier camera (FIG. 4A).

The rDLW printer 400 includes a laser source (e.g., laser system) 424 which produces the laser beam 404 (FIG. 4A). In some embodiments, the laser source 424 can provide the laser beam 404 at about a 120 fs pulse duration and 80 Mhz repetition. For example, the laser source 424 can provide the laser radiation for both polymerization and visualization of the photoresist and printed objects/structures. In some embodiments, beam intensity of the laser beam 404 can be modulated by the power modulator 412, which can be configured as a Pockels cell (FIG. 4A)

In some embodiments, to flatten the profile and improve collimation of the laser beam 404, the laser beam 404 can be routed through a beam expander 428 before entering the optics of the resonant raster scanner 410.

The rDLW printer (or printer system) 400 can comprise a control system 434. The control system can comprise a data acquisition system that interfaces the above-described components of the rDLW printer with a processor and memory (e.g., data storage) of the control system 434. The memory of the control system 434 can include computer-readable instructions for converting a received CAD model (e.g., via a received stereolithography (STL) file) of a desired 3D structure to be printed into commands or actuation signals sent from the processor of the control system 434 to the components of the rDLW printer (e.g., the laser source 424, power modulator 412, piezo-scanner 416, and/or the like). Thus, the rDLW printer 400 can 3D print the 3D structure defined in the received computer model.

As a result, the rDLW printer 400 can be capable of printing (referred to herein as 3D printing) complex, micron-scale structures efficiently and at a high resolution. For example, in some embodiments, the resonant raster scanner 410 of the rDLW printer 400 can scan at approximately 8 kHz, thereby bringing the rDLW printer's speed up to about 8,000 mm/s. This print speed can be tens to thousands of times faster than other high-speed galvanometer based DLW printers. As introduced above, the increased scanning speed of the rDLW printer 400 can reduce an amount of time for polymerization of the polymer liquid (e.g., photoresist) in the build envelope 406 to occur, as well as allowing for a reduction in energy being delivered to the polymer liquid during each pass of the laser beam 404. This can result in more robust 3D structures which adhere better to the underlying substrate.

In other embodiments, the 3D printing at 304 can be performed with another type of 3D printing device.

Returning to FIG. 3, the method at 304 can include receiving a CAD model (e.g., via a STL file) at the processor of the control system of the 3D printer (e.g., the control system 434 of the rDLW printer 400 shown in FIG. 4A). The received CAD model can define a specified (predefined) 3D structure to be printed onto the substrate.

The method at 304 can further include actuating the 3D printer, via electrical signals sent to components of the 3D printer from the control system, to print the predetermined 3D structure onto the substrate, layer by layer. As an example, by utilizing 3D printing with the above-described rDLW printer to print 3D structures defined by a received computer model, a wide variety of print geometries with intricate features (e.g., pores, internal channels, hook features, mosquito proboscis-like tips, and the like) are possible in a reduced time frame (as compared to other microfabrication processes, such as MEMS, which may utilize sequences of layering, masking, and etching to produce multi-layer structures, but in a much more time intensive, complex, and expensive manner). Further, by utilizing 3D printing to create the 3D structures for the electrodes, the electrodes of a multielectrode array can be customized for any application. For example, almost limitless (for the space allowed by a print pad on the substrate) geometries can be created in a CAD file and then printed by the 3D printer in a rapid manner. Thus, method 300 can be adaptable to a wide variety of application, including different implantation locations in the body and for stimulating/recording different types or locations of tissue in the body.

Examples of 3D structures that can be printed on a substrate (e.g., a thin film substrate) and metalized to form a 3D electronic device (according to method 300) are discussed further below with reference to FIGS. 8A-11C, 13-15, 17-19, 23, 24, 30A, and 30B.

In some embodiments, the resulting 3D printed structures formed at 304 can be comprise (e.g., composed of) a photopolymer. Further, in some embodiments, the resulting 3D printed structures formed at 304 can comprise a photopolymer and can have an aspect ratio of at least 10:1. In still other embodiments, the resulting 3D printed structures formed at 304 can comprise a photopolymer and can comprise a plurality of pores.

At 306, method 300 includes selectively metalizing the 3D printed structure(s) on the substrate using photolithography techniques to form a 3D electronic device (e.g., such as the 3D multielectrode array 200 of FIG. 2 or other 3D electronic devices and multielectrode arrays discussed herein). As used herein, "selective metallization" of the 3D printed structure(s) can refer to applying (e.g., via sputtering) metal to the surface of the 3D printed structure(s) while not applying metal to a portion of the surface of the substrate surrounding the 3D printed structure(s). As a result, multiple electrodes or electrical components on the substrate can be isolated, separated, and/or insulated from one other, thereby avoiding shorts in the 3D electronic device. For example, as used herein, an electrode or electrical component (e.g., selectively metallized 3D structures) being "electrically isolated" from adjacent electrodes or electrical components may refer to the electrode or electronic component relaying an electrical signal along a designated path (e.g., electrical contact) and not having electrical communication (e.g., not sending or receiving electrical signals) with adjacent electrodes or electrical components. In this way, an array of multiple electrically isolated electrodes can send a plurality of separate electrical signals that do not interfere with one another. In some embodiments, adjacent electrodes or electrical components can be electrically isolated from one another by an insulating layer of the 3D electronic device.

In some embodiments, the selective metallization at 306 can include, at 308, implementing a positive photoresist lithography process (e.g., a proximity print photolithography process using a positive photoresist) to selectively metallize the 3D printed structure. FIG. 5 is a schematic showing an exemplary process 500 for implementing such a positive photoresist lithography process to selectively metallize the 3D printed structure.

As shown in FIG. 5, at 502, a 3D structure 514 has been printed (e.g., via the 3D printing at 304 of method 300) onto a portion of a substrate 516 that is directly adjacent to an electrical contact or metal trace 518. In some embodiments, the 3D structure 514 can be printed directly onto the substrate 516, via an open window to the substrate 516 (e.g., such as window 1228 shown in FIGS. 12A and 12B) which is directly adjacent to the metal trace 518.

In some examples, the metal trace 518 can extend from the 3D structure 514, along a portion of the substrate 516 and to a connection end of the substrate that can be electrically connected to another electronic component or electrical source.

In FIG. 5, the 3D structure 514 has a tapered (e.g., conical or pyramidal) shape. However, it should be noted that this shape of the 3D structure 514 is exemplary and other geometries for the 3D structure 514 are possible (e.g., mesh, rectangular, dome-shaped, and the like).

As shown at 502, a surface of the substrate 516 surrounding the 3D structure 514 does not include exposed metal traces. As such, the final metallized 3D structure (e.g., as shown at 512, as discussed further below) can be insulated from additional, adjacent metallized 3D structures or components of the electronic device. For example, in some embodiments, the final 3D electronic device can be a multielectrode array comprising multiple 3D electrodes (e.g., multiple metallized 3D structures).

At 504, a positive photoresist (PR) 520 can be spun onto an entire surface of the substrate 516, including the 3D structure 514. A photoresist is a light sensitive polymer that can be used in standard photolithography.

At 506, a proximity mask 522 is positioned over (e.g., vertically above) the substrate 516 and the entire surface covered by the positive photoresist 520 is exposed to a light source (e.g., radiation, such as UV radiation) 524. For example, in some embodiments, at 506, radiation is applied to the applied layer of positive photoresist 520.

As shown at 506 in FIG. 5, the proximity mask 522 includes a window or opening 526 that can be arranged directly (in a vertical direction) over the 3D structure 514 and sized such that only a portion 528 of the positive photoresist 520 that covers the 3D structure is exposed to the radiation of the light source 524.

The positive photoresist 520 becomes more soluble after exposure to the light source 524 (e.g., after being exposed to radiation). Thus, as shown at 508, when the positive photoresist 520 on the substrate 516 is exposed to a developer solution (e.g., via submersion, washing, or the like), the portion 528 of the positive photoresist 520 that was exposed to the light source 524 and that covers the 3D structure 514 is removed or washed away. As shown at 508, this leaves the 3D structure 514 uncovered while a remainder of the substrate 516 (e.g., at least the portion shown in FIG. 5 and surrounding the 3D structure) remains covered by the positive photoresist 520.

At 510, metal is then sputtered over the surface of the device (e.g., the remaining positive photoresist 520 and the exposed 3D structure 514), thereby forming a metal layer 530 over the remaining positive photoresist 520 and the 3D structure. The metal can comprise platinum, titanium, gold, or the like.

After metallization, as shown at 512, the remaining positive photoresist is removed (e.g., lifted off the substrate 516), thereby revealing a selectively metallized 3D printed 3D structure 532 that is electrically connected to the metal trace 518. The metallized 3D printed 3D structure 532 is in electrical contact with the metal trace 518 due to the sputtered metal material covering a portion of the 3D structure (e.g., its base) that is in direct contact with the metal trace 518. In some embodiments, the metallized 3D printed 3D structure 532 is in electrical contact with the adjacent metal trace 518 due to the sputtered metal material covering a portion of the 3D structure (at its base) that is in direct contact with the metal trace 518 and/or the sputtered metal covering a portion of the substrate 516 bridging a gap between the metallized 3D printed structure 532 and the adjacent metal trace 518, thereby electrically connecting the metallized 3D printed 3D structure 532 (e.g., the electrode) and the metal trace 518.

The resulting device shown at 512 in FIG. 5 can be a 3D electronic device 534, as described herein. In some embodiments, the metallized 3D printed 3D structure 532 can be one electrode of a multielectrode array.

Returning to FIG. 3, in some embodiments, the selective metallization at 306 can include, at 310, implementing a negative photoresist lithography process (e.g., a proximity print photolithography process using a negative photoresist) to selectively metallize the 3D printed structure. FIG. 6 is a schematic showing an exemplary process 600 for implementing such a negative photoresist lithography process to selectively metallize the 3D printed structure.

Figure 6:
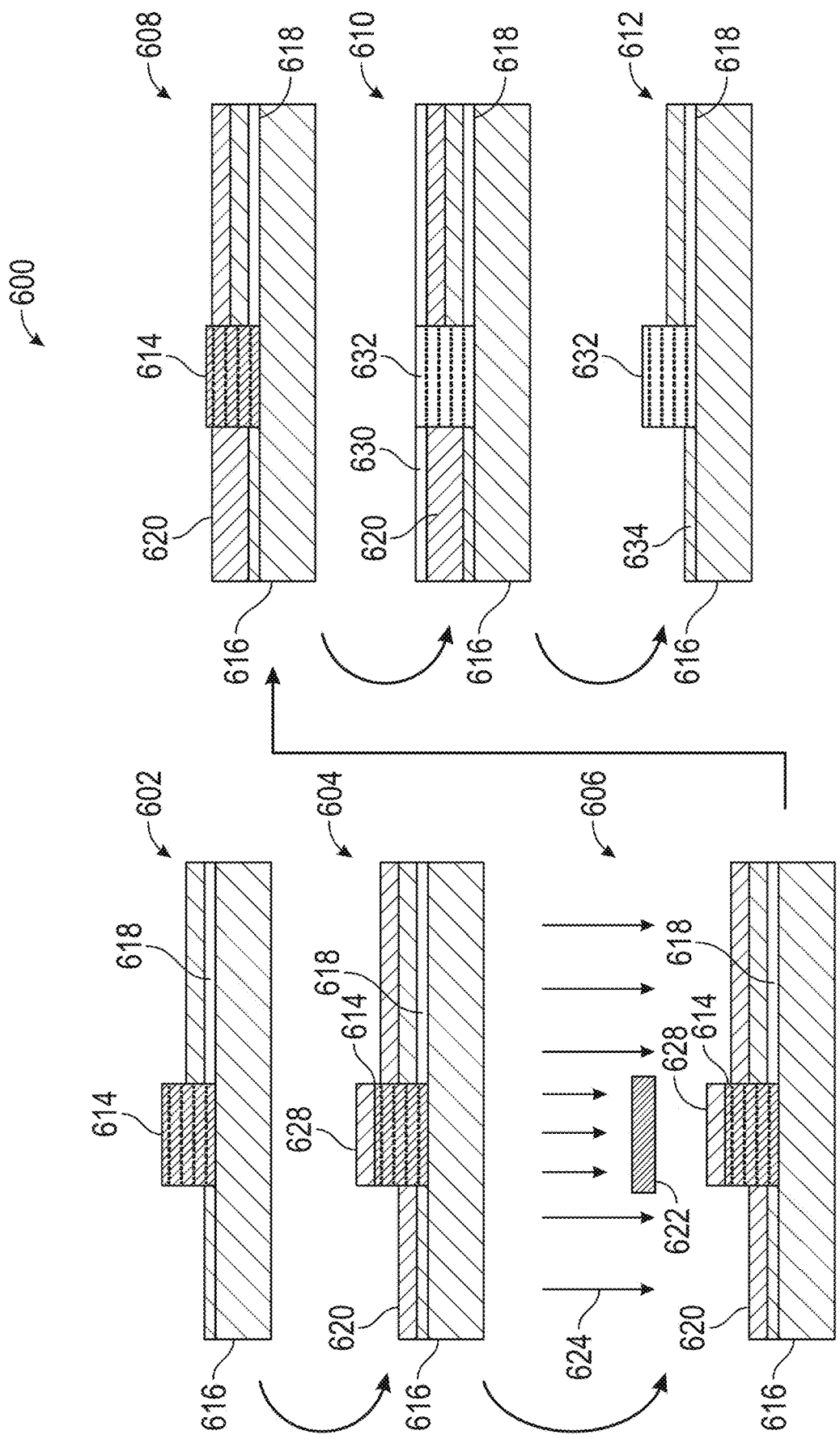
FIG. 6 is a schematic showing an exemplary process for implementing a negative photoresist lithography process to selectively metallize a 3D printed structure.

As shown in FIG. 6, at 602, a 3D structure 614 has been printed (e.g., via the 3D printing at 304 of method 300) onto a portion of a substrate 616 that is adjacent to an electrical contact or metal trace 618. For example, the 3D structure 614 can be printed directly onto the substrate 616, via an open window to the substrate 616 (e.g., such as window 1228 shown in FIGS. 12A and 12B) which is directly adjacent to the metal trace 618.

The exemplary 3D structure 614 shown in FIG. 6 can have a woodpile or mesh structure. However, in other embodiments, the 3D printed 3D structure 614 can have a different geometry and/or geometrical features, such as having a conical shape, dome shape, pyramidal shape, and the like.

In some embodiments, as shown in FIG. 6, the metal trace 618 can extend from next to the 3D structure 614, along a portion of the substrate 616 and to a connection end of the substrate that can be electrically connected to another electronic component or electrical source. As shown at 602, a surface of the substrate 616 surrounding the 3D structure 614 does not include exposed metal traces (as described above with reference to FIG. 5).

At 604, a negative photoresist (PR) 620 can be spun onto an entire surface of the substrate 616, including the 3D structure 614. At 606, a proximity mask 622 is positioned over (e.g., vertically above) the 3D structure 614 and a portion 628 of the negative photoresist 620 that covers the 3D structure 614.

Specifically, as shown in FIG. 6, the proximity mask 622 is positioned and sized such that it covers only the portion 628 of the negative photoresist 620 which covers the 3D structure 614. A remainder of the negative photoresist 620 (e.g., a portion of the negative photoresist 620 that covers the surface of the substrate 616) is not covered by the proximity mask 622.

After positioning the proximity mask 622 at 606, the negative photoresist 620 is exposed to a light source (e.g., radiation, such as UV radiation) 624, with the proximity mask 622 blocking the radiation from the light source 624 from reaching the portion 628 of the negative photoresist 620 that covers the 3D structure 614. The remainder of the negative photoresist 620 that covers the substrate 616 only (and not the 3D structure 614) is exposed to the radiation from the light source 624.

In contrast to the positive photoresist used in the process 500 of FIG. 5, the negative photoresist 620 becomes less soluble after exposure to the light source 524. Thus, as shown at 608, when the negative photoresist 620 on the substrate 616 is exposed to a developer solution (e.g., via submersion, washing, or the like), the portion 628 of the negative photoresist 620 that was blocked from the light source 624 (e.g., unexposed due to the positioning of the proximity mask 622) and that covers the 3D structure 614 is removed.

As shown at 608, this leaves the 3D structure 614 uncovered while a remainder of the substrate 616 (or at least the portion shown in FIG. 6 and surrounding the 3D structure) remains covered by the negative photoresist 620.

At 610, metal is then applied (e.g., sputtered) over the surface of the device which includes the remaining negative photoresist 620 and the exposed 3D structure 614, thereby forming a metal layer 630 over the remaining negative photoresist 620 and the 3D structure 614. The metal can comprise platinum, titanium, gold, or the like.

After metallization, as shown at 612, the remaining negative photoresist 620 is removed (e.g., lifted off the substrate 616), thereby revealing a selectively metallized 3D printed 3D structure 632 adjacent to the metal trace 618. The resulting device shown at 612 in FIG. 6 can be a 3D electronic device 634 (or a portion of a 3D electronic device), as described herein.

Figure 7:
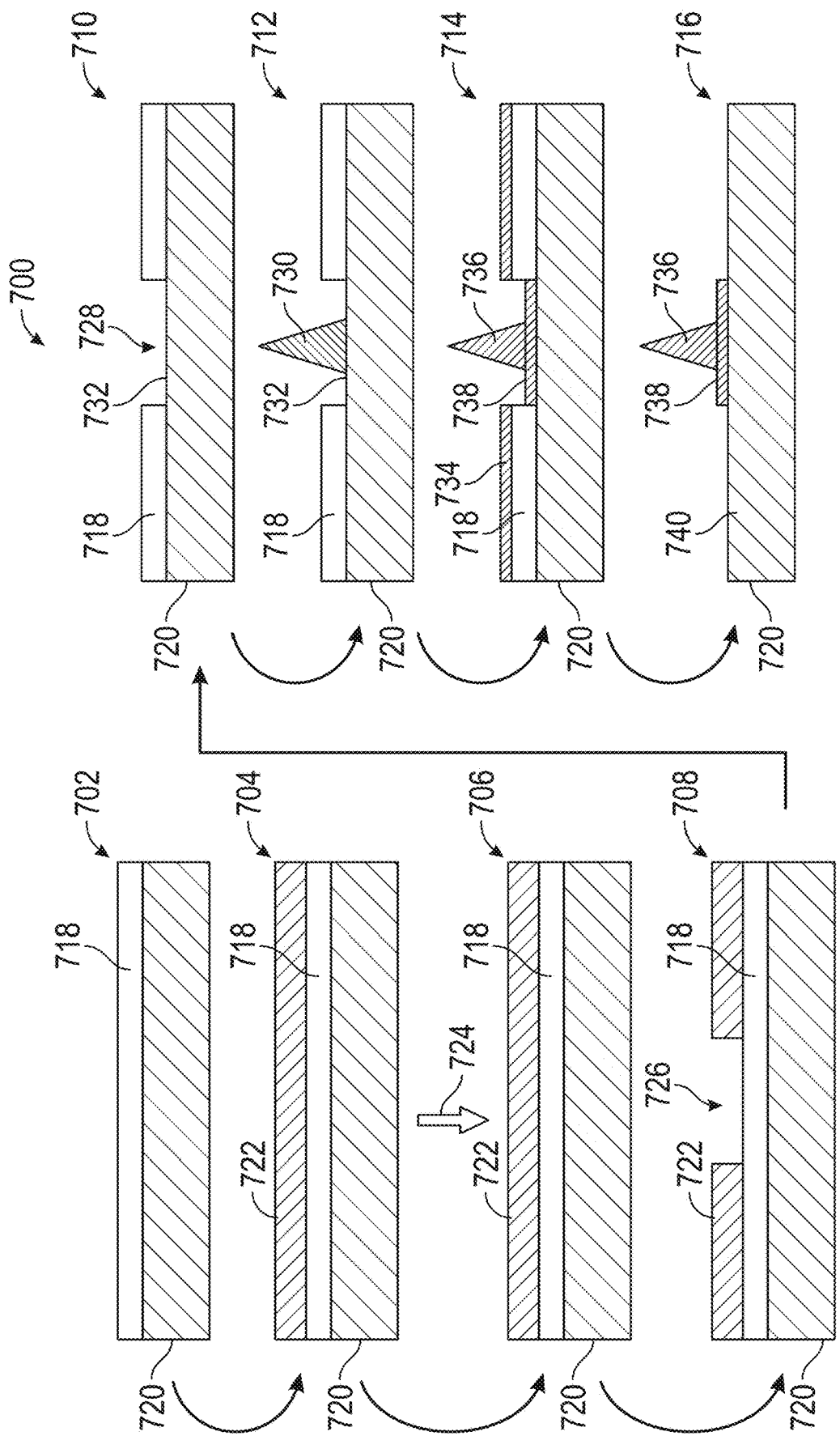
FIG. 7 is a schematic showing an exemplary process for preparing a substrate to receive a 3D printed structure and implementing a sacrificial layer and photoresist lithography process to selectively metallize the 3D printed structure.
Figure 28:
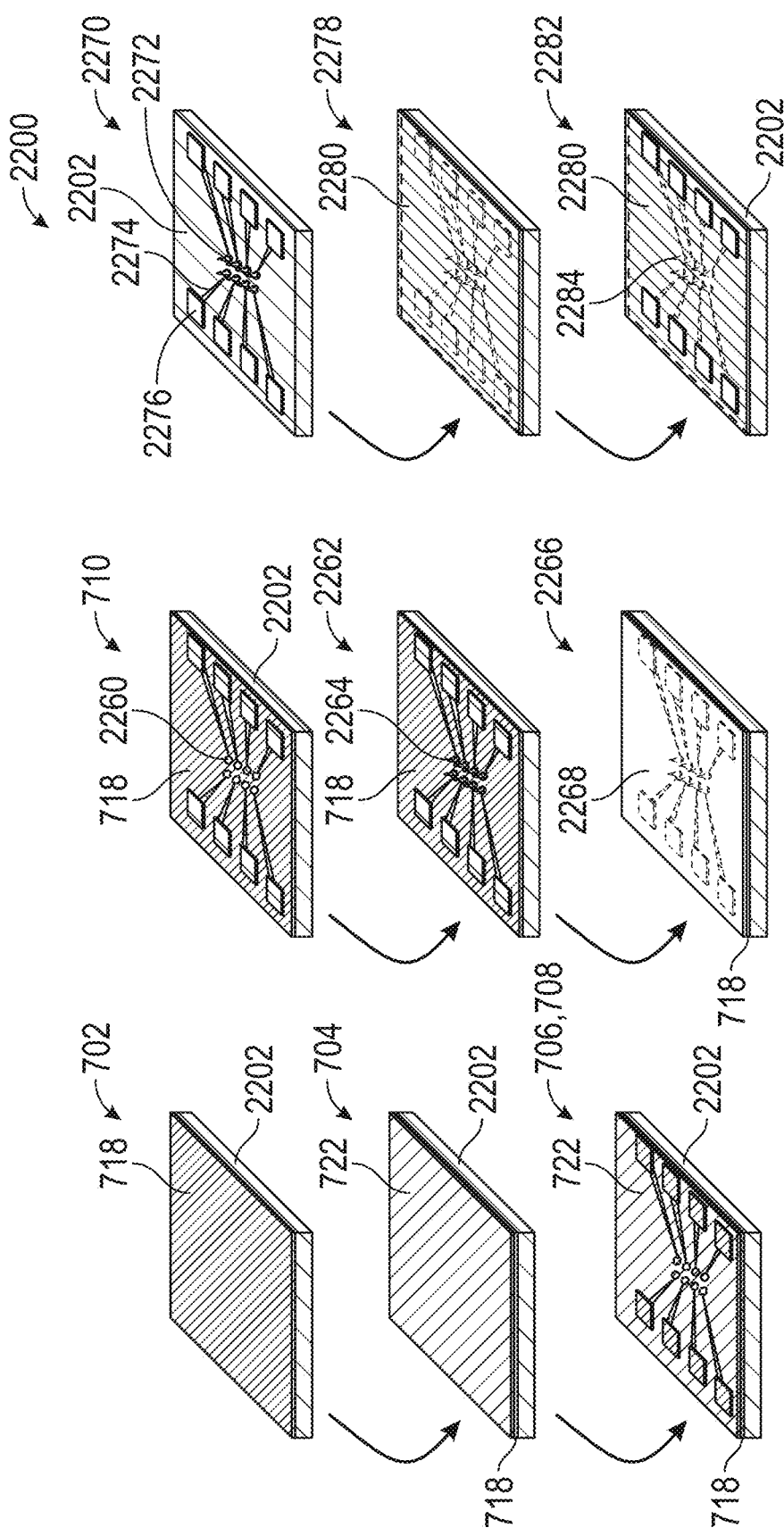
FIG. 28 is a schematic showing an exemplary process for fabricating a fully metallized and insulated 3D multielectrode array with metallized 3D printed structures that are electrically connected to predefined electrical traces and contacts of the device, where each metallized 3D printed structure is covered by an insulating material, except for an exposed, metallized tip.
Figure 29:
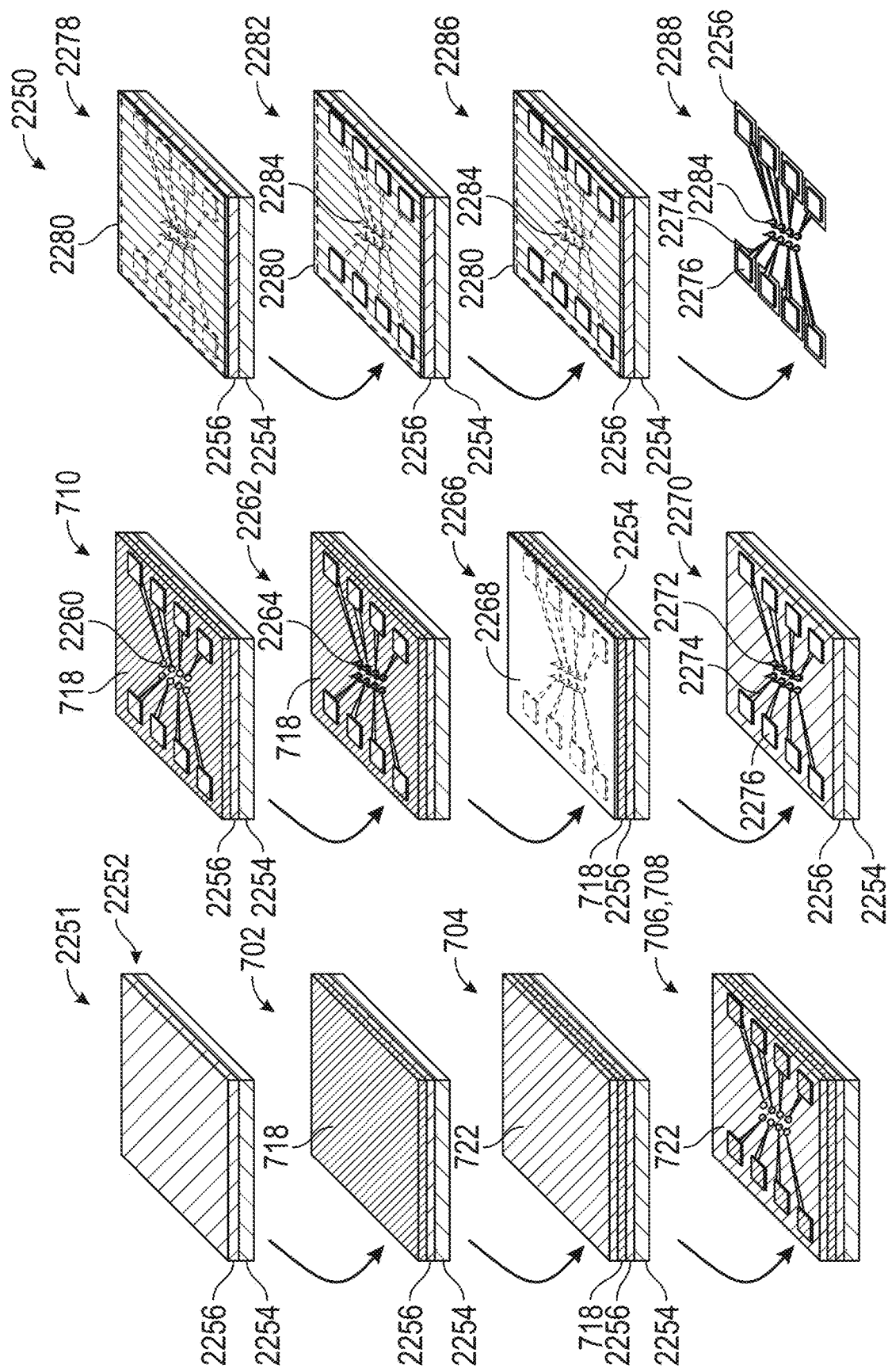
FIG. 29 is a schematic showing another exemplary process for fabricating a fully metallized and insulated 3D multielectrode array with metallized 3D printed structures that are electrically connected to predefined electrical traces and contacts of the device, where each metallized 3D printed structure is covered by an insulating material, except for an exposed, metallized tip, and where the substrate of the device is a thin film material.

Returning to FIG. 3, in some embodiments, the selective metallization at 306 can include, at 312, utilizing a sacrificial metal layer and photoresist lithography process to selectively metallize the 3D printed structure. FIG. 7 is a schematic showing an exemplary process 700 for preparing a substrate to receive the 3D printed structure and implementing such a sacrificial layer and photoresist lithography process to selectively metallize the 3D printed structure. Similar processes to that of FIG. 7, for making a 3D multielectrode array, are shown in FIGS. 28 and 29, as described in greater detail below.

As shown in FIG. 7, at 702, a sacrificial metal layer 718 can be applied, via sputtering, onto a surface of a substrate 720. In some embodiments, the sacrificial metal layer can comprise aluminum or chromium. Then, at 704, a positive photoresist 722 is spun onto the surface of the sacrificial metal layer 718, thereby covering the sacrificial metal layer 718.

At 706, a UV light source 724 (e.g., a 405 nm laser writer or a mercury lamp) can be directed at the device and used to expose and trace specified regions of the positive photoresist 722 which cover a portion of the substrate 720 where electrical contacts and the 3D printed structure are desired to be positioned. Said another way, the UV light source 724 can be used at 706 to etch or trace (e.g., raster scan) and define a desired location for the electrical contacts, traces, and/or 3D printed structure(s) on the substrate 720.

At 708, the positive photoresist 722 on the substrate 720 is exposed to a developer solution (e.g., via submersion, washing, or the like). As a result, the portions of the positive photoresist 722 that were exposed to the UV light source 724 are removed, leaving behind an opening (or window) 726 in the positive photoresist 722 to the underlying sacrificial metal layer 718.

At 710, the device is exposed to an acidic metal etchant, thereby removing a portion of the sacrificial metal layer 718 that is exposed by the opening 726. In this way, the positive photoresist 722 can serve as an etch mask for the sacrificial metal layer 718 in the acidic metal etchant. The remaining positive photoresist 722 can then be removed by exposure to a developing solution (e.g., developer). As a result, an opening 728 in the sacrificial metal layer 718 to the underlying substrate 720 is exposed, thereby exposing a selected portion or exposed portion 732 of the substrate 720. In some embodiments, as described herein with reference to FIGS. 12A and 12B, the substrate 720 can comprise preconfigured and photopatterned metal traces and/or electrical contacts and the methods at 706, 708, and 710 can be used to etch through the sacrificial metal layer 718 to expose the underlying electrical traces and/or electrical contacts, as well as print pads on the substrate 720 for receiving a 3D printed structure.

At 712, a 3D structure 730 can then be printed (e.g., via the 3D printing at 304 of method 300) onto the exposed portion 732 of the substrate 720. In FIG. 7, the 3D structure 730 has a conical or pyramidal shape. However, it should be noted that this shape of the 3D structure 730 is exemplary and other geometries for the 3D structure 730 are possible (e.g., mesh, rectangular, dome-shaped, and the like).

At 714, metal is then sputtered over the surface of the device (e.g., the remaining sacrificial metal layer 718 and the exposed 3D structure 730), thereby forming a metal layer 734 over the remaining sacrificial metal layer 718 and the 3D structure 730. The metal can comprise platinum, titanium, gold, or the like.

After metallization, as shown at 716, the remaining sacrificial metal layer 718 is removed (e.g., lifted off the substrate 720), thereby revealing a selectively metallized 3D printed 3D structure 736 with electrical contacts (e.g., metal traces) 738. The resulting device shown at 716 in FIG. 7 can be a 3D electronic device 740 (or a portion of a 3D electronic device), as described herein.

The electrical contacts 738 can be in direct contact (and thus in electrical contact and communication) with predefined metal traces and contacts, such as those shown in FIGS. 12A, 12B, 28, and 29, as introduced above. For example, as shown at 1208 in the method of FIGS. 12A and 12B, which can be similar to the method of FIG. 7, the windows 1228 (e.g., exposed portions of the substrate 1220) are connected to (e.g., arranged adjacent to) the pre-photopatterned (as described above) traces 1224 and electrical contacts 1222. Thus, after 3D printing a 3D structure 1232 into each of the windows 1228, onto each of the exposed portions of the substrate 1220 or substrate 1205 (as shown at 1214 in FIG. 12A or 12B), sputtering the entire surface with metal to form a top metal layer 1234 (as shown at 1216 in FIGS. 12A and 12B), and then lifting off the sacrificial metal layer 1230, metallized 3D printed structures 1236 that are in direct electrical contact with the predefined traces 1224 and electrical contacts 1222 are produced (as shown at 1218 in FIGS. 12A and 12B). The resulting device at 1218 is a fully metallized and insulated device with metallized 3D printed structures 1236 that can function as 3D electrodes or other 3D electrical components, as described herein. In some examples, the method can further continue to 1240 to release the full device (multielectrode array) from the silicon wafer 1203 (e.g., using a laser), thereby resulting in the 3D multielectrode array 1242 comprising a thin film, polyimide base or substrate (FIG. 12B).

FIGS. 28 and 29, which are described in greater detail below, can follow a similar process to that of FIG. 7 and result in the production of a thin film multielectrode array comprising 3D printed electrodes that are electrically isolated from one another and the environment, except for exposed metallized tips of the 3D printed electrodes. For example, the sacrificial metal layer can be sputtered onto a polyimide (thin film) surface or layer on a silicon wafer (or other substrate) and then the finalized multielectrode array can be released from the underlying wafer (see further description below with reference to FIG. 29). Additionally, in some examples, the method at 312 can include applying an insulating later to the device (e.g., insulating layer 2280 shown at 2278 in FIGS. 28 and 29) and then removing the insulating layer from only the tips of the metallized 3D printed structures, thereby exposing metallized tips of the metallized 3D printed structures while a remainder of the device remains coated with the insulating layer (as shown at 2282 in FIGS. 28 and 29). As a result, the final device can include a plurality of electrodes and electrical traces that are electrically isolated (or insulated) from each other and from the environment, except for the exposed metallized tips of the 3D electrodes.

Figure 13:
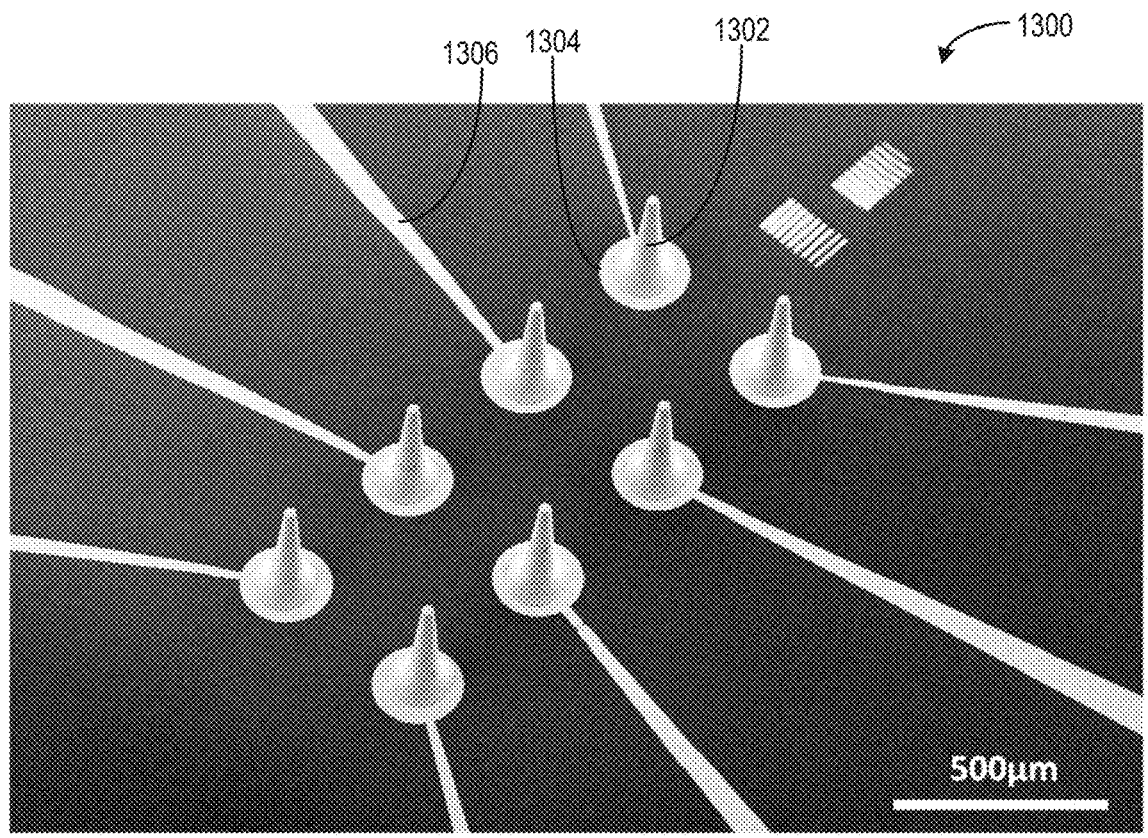
FIG. 13 is a detail view of an exemplary 3D multielectrode array comprising metallized 3D structures that are printed onto electrical contacts or pads which are directly connected to predefined electrical traces.

FIG. 13 shows a detail view of an exemplary device 1300, which can be configured as a multielectrode array, comprising metallized 3D structures 1302 that are printed onto windows or pads 1304 of a substrate which are directly connected to electrical traces 1306 which can extend to individual electrical contacts (e.g., similar to contacts 1222 shown in FIGS. 12A and 12B). The device 1300 can be formed using the methods described above with reference to FIGS. 3, 7, 12, 28, and/or 29. In some embodiments, the substrate, and thus the pads 1304 can comprise silicon.

In some embodiments, the metallized 3D structures 1302 can be configured as spike electrodes, as described further below with reference to FIG. 9A-11C, 23, or 30A. In other embodiments, as shown in the exemplary embodiment of FIG. 14, a device which can be configured as a multielectrode array 1400 can comprise more cuboidal, mesh-like or porous structures (similar to the mesh or porous structures 800, 804, and 806 shown in FIGS. 8A-8C, as described below) which can be metallized using one of the processes described herein to form a plurality of 3D electrodes. More specifically, the multielectrode array 1400 can comprise photopatterned electrical traces 1402 extending to print pads 1404 on a substrate (e.g., thin film substrate) 1406. 3D cuboidal and/or porous (or mesh) structures can be 3D printed onto the print pads 1404 and selectively metallized, as described herein, to form 3D electrodes 1408, 1410, 1412.

Figure 14:
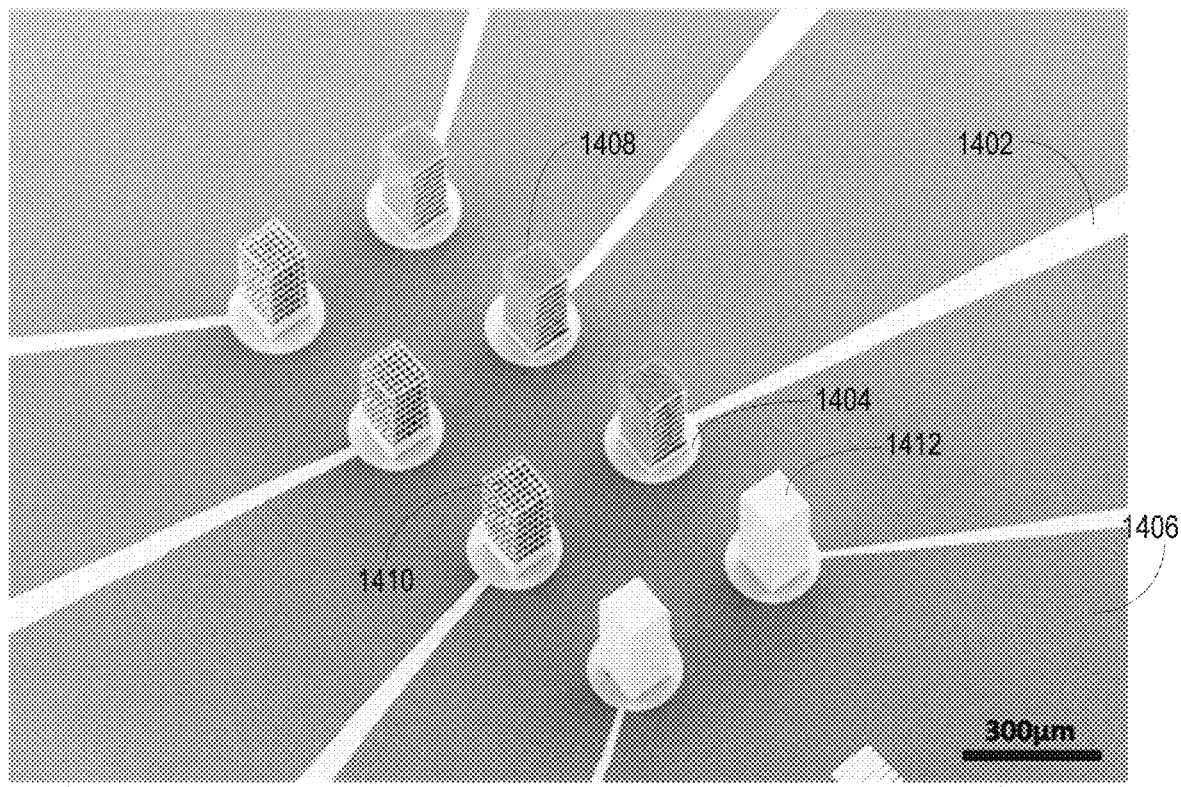
FIG. 14 is a detail view of an exemplary 3D multielectrode array comprising a plurality of 3D electrodes, some of which have different 3D printed structures than other of the 3D printed electrodes.

FIG. 14 shows an exemplary embodiment of the multielectrode array 1400 comprising a plurality of 3D electrodes, some of which have different 3D printed structures. For example, FIG. 14 shows a first 3D electrode 1408 that is cuboidal with a first porous (mesh) structure, a second 3D electrode 1410 that is cuboidal with a second porous (mesh) structure, and a third 3D electrode 1412 that is cuboidal with a third structure that may not be porous or may have a very small (and not visible) pore size. The first porous structure of the first 3D electrode 1408, the second porous structure of the second 3D electrode 1410, and the third structure of the third 3D electrode may have different pore sizes, shapes, and/or spacing relative to one another.

In this way, 3D printing, in combination with the metallization methods described herein can easily and quickly produce a single multielectrode array 1400 with differently shaped or configured (e.g., different size and pattern of pores) 3D electrodes 1408, 1410, and 1412. In other embodiments, the differently configured 3D electrodes 1408, 1410, and 1412 can be included on separate multielectrode arrays which are specified for different applications. Thus, a wide variety of 3D electrode structures for multielectrode arrays are possible and can be selected based on a specified application.

In some embodiments, the multielectrode array 1400 (as well as device 1300 of FIG. 13) can be formed by a portion of the method presented in FIG. 12A but may not be insulated. Thus, fabricating these devices does not include the insulating step at 1206 and photolithography step at 1208 in the method presented in FIG. 12A.

Figure 15:
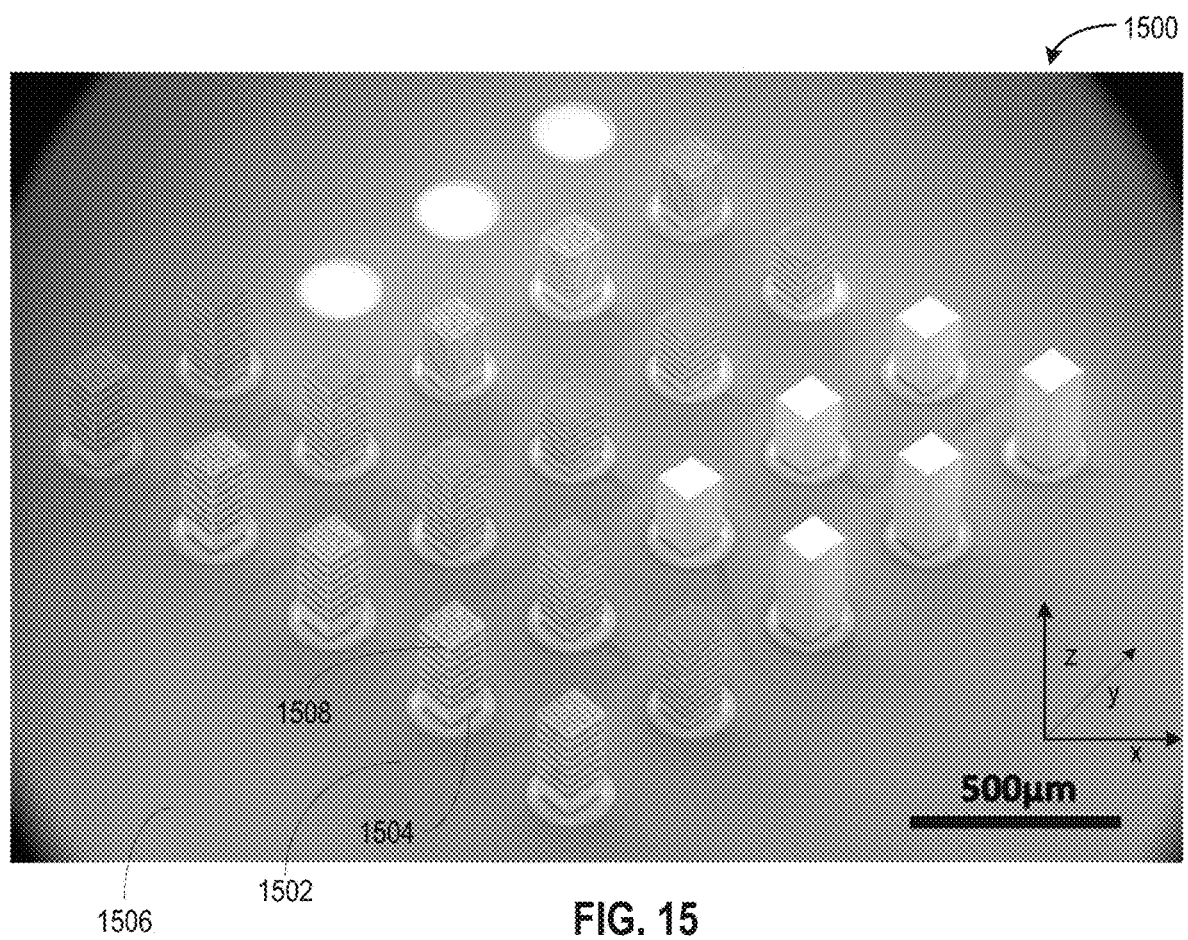
FIG. 15 is a detail view of an exemplary insulated multielectrode array comprising photopatterned electrical traces extending to print pads on a substrate, where the substrate and electrical traces are covered by an insulating layer, and a plurality of 3D printed electrodes.

However, it is possible to fabricate these devices to be insulated, as presented at the method of FIG. 12A. For example, FIG. 15 shows an exemplary insulated multielectrode array 1500 comprising photopatterned electrical traces 1502 extending to print pads 1504 on a substrate (e.g., thin film substrate), where the substrate and electrical traces 1502 are covered by an insulating layer 1506. As a result, the electrical traces 1502 are separated and electrically insulated from one another and isolated from the environment. Similar to the multielectrode array 1400 of FIG. 14, the multielectrode array 1500 comprises a plurality of 3D electrodes 1508 having different structures (e.g., different heights in the z-direction, different pore sizes and patterns, and the like). In some embodiments, having 3D electrodes 1508 with different heights on the same multielectrode array 1500 can allow for a single array to address different areas (and depths) in a tissue when implanted (e.g., in the brain).

Figure 16:
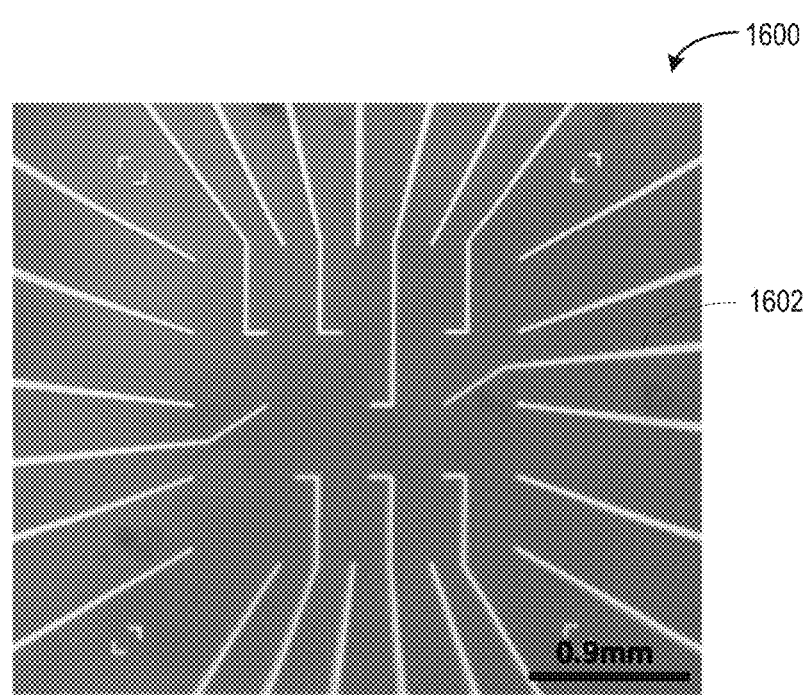
FIG. 16 is a view of an exemplary arrangement of electrical traces on a substrate which can be used for a multielectrode array.

An exemplary arrangement of electrical traces 1602 on a substrate 1600, which can be used for any of the multielectrode arrays described herein is shown in FIG. 16. The traces 1602 can also be referred to herein as interconnects. As described above, the traces 1602 can be photopatterned onto the substrate 1600 using photolithography. In some embodiments, the traces 1602 (and other metal traces described herein) can be photopatterned as three sequential layers of Titanium (in some embodiments about 10 nm thick), Platinum (in some embodiments about 50 nm thick), and Titanium (in some embodiments about 10 nm thick), respectively. For example, the photopatterning of the traces 1602 can include a three-step sputter process where Titanium is used as an adhesion layer for the Platinum to the substrate 1600 below and the insulating material (e.g., insulating layer 1506 of FIG. 15) above.

FIGS. 8A-11C show exemplary 3D structures that can be 3D printed using 3D printing, as described above (e.g., using a rDLW printer, such as the rDLW printer 400 shown in FIG. 4). In some embodiments, the 3D structures can be composed of a photopolymer (e.g., a plurality of stacked layers of photopolymer formed into a desired 3D structure).

The 3D structures shown in FIGS. 8A-11C, as well as the fabrication methods and 3D electronic devices described herein, can be used in a variety of applications. For example, the methods and the 3D structures for the fabricated 3D electronic devices described herein can be used to fabricate small, implantable electronic devices (e.g., electrodes and multielectrode arrays) and/or 3D electronics for smaller-scale applications, such as computer chips.

As one example, implantable, 3D electrodes or multielectrode arrays comprising multiple 3D electrodes formed from metallized, 3D printed structures (e.g., as shown in FIG. 2B) can be formed via the fabrication methods described herein. These implantable 3D electrodes or multielectrode arrays can be used in a variety of neural applications within the body, such as in the heart, brain, spinal cord, and the like.

While the 3D printed, 3D structures shown in FIGS. 8A-11C may be discussed below as being used for implantable electrode applications, it should be noted that these 3D structures, and/or similar 3D structures, can be used in other 3D electronic devices, such as computer chips and other small (e.g., micron) scale electrical applications and/or for in vitro applications such as in vitro cell culture. In such embodiments, the 3D structures can be 3D printed and metallized on substrates, using the processes described above with reference to FIGS. 3, 5-7, and 12, to form electronic devices with one or more metallized 3D structures that extend outward from a more planar substrate and that can be used for enhanced electrical communication and/or penetration into a tissue.

Further, the 3D structures shown in FIGS. 8A-11C can be configured with a relatively high surface area, surface area to footprint ratio, and/or aspect ratio. As used herein, a "high surface area" of the 3D printed, 3D structures can refer to an overall contact surface area of the 3D structure, which may include an internal surface area created by pores, spaces, or channels in the structure. Further, a "high" surface area or "relatively high" surface area, as used herein with reference to the various 3D structures, can refer to a high surface area to footprint ratio as compared to a more 2D, planar structure (e.g., a single layer or small number of layers of material on a substrate, which can be formed via more traditional photolithography techniques alone). The "footprint" of the 3D structure can refer to the 2D surface area that the 3D structure occupies on a substrate or base material. In this way, by having a more 3D structure that extends away from the substrate (e.g., in the z direction shown in FIGS. 8A, 9A, 10A, and 11A) and that includes one or more internal channels or pores that are accessible from an exterior of the 3D structure, a larger surface area to footprint ratio is created.

Additionally, in some embodiments, the 3D structures shown in FIGS. 8A-11C (and in the arrays of FIGS. 13-15) can be referred to as having a height (along the z-axis) and/or aspect ratio greater than a threshold value (e.g., one, 5:1, 7:1, 8:1, or 10:1). As defined above, the aspect ratio can be defined as a ratio of the height (along the z-axis) of the 3D structure to a width or diameter of the 3D structure (along an x or y-axis). For example, for a cuboid structure, such as those shown in FIGS. 14 and 15, the aspect ratio may be a ratio of the height of the 3D structure (in a direction that is normal to the substrate, such as the z direction shown in FIG. 15) to a width of the 3D structure. In some embodiments, the height or aspect ratio of the 3D structure can be selected such that a 3D electrode with the 3D structure can penetrate a specified depth into a tissue in which the device or multielectrode array is implanted.

In some embodiments, the 3D structures described herein can have a surface area to footprint ratio greater than one (e.g., 1:1). In some embodiments, the 3D structures described herein can have a surface area to footprint ratio greater than two (e.g., 2:1). In some embodiments, the 3D structures described herein can have a surface area to footprint ratio in a range of 1.2 to 10 (e.g., 1.2:1 to 10:1), 1.5 to 5 (e.g., 1.5:1 to 5:1), 1.8 to 5 (e.g., 1.8:1 to 5:1), or 2 to 10 (e.g., 2:1 to 10:1). In some embodiments, the 3D structures described herein can have an aspect ratio of at least 1:1, of at least 5:1, of at least 7:1, of at least 10:1, of at least 20:1, up to 40:1 or between 3:1 and 40:1 or 10:1 and 40:1.

Figure 8A:
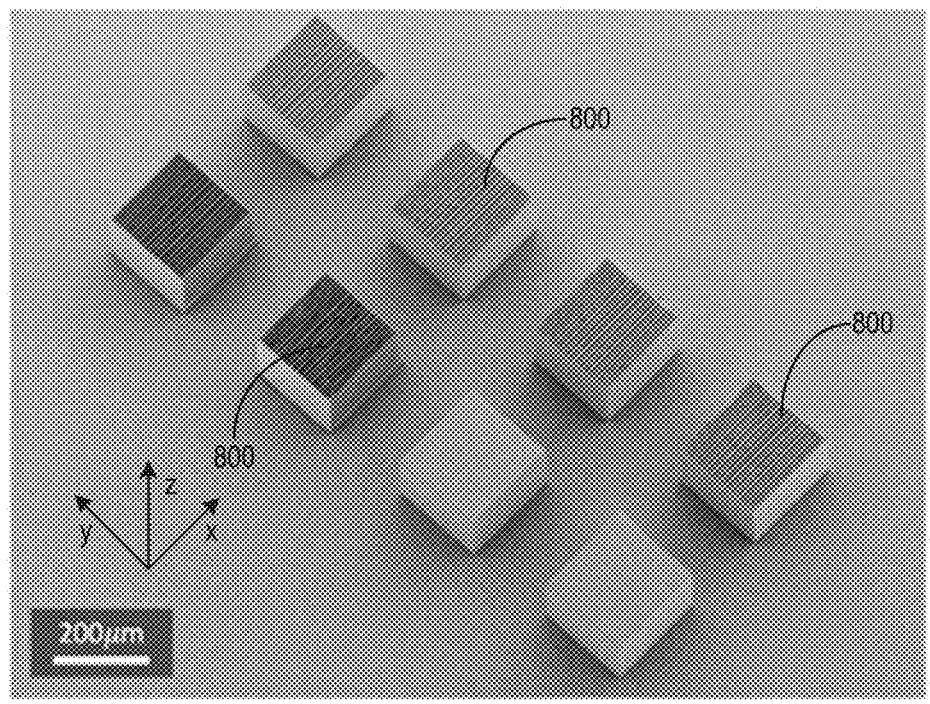
FIG. 8A is a perspective view of various 3D printed, mesh structures that are configured with a high surface area to footprint ratio and a porous or mesh-like structure and which can be part of a 3D electronic device.
Figure 8B:
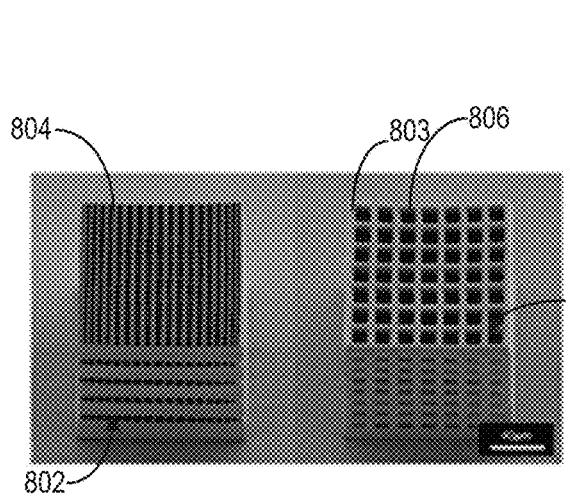
FIG. 8B shows a zoomed-in view of two 3D printed mesh structures of FIG. 8A with different pore sizes.
Figure 8C:
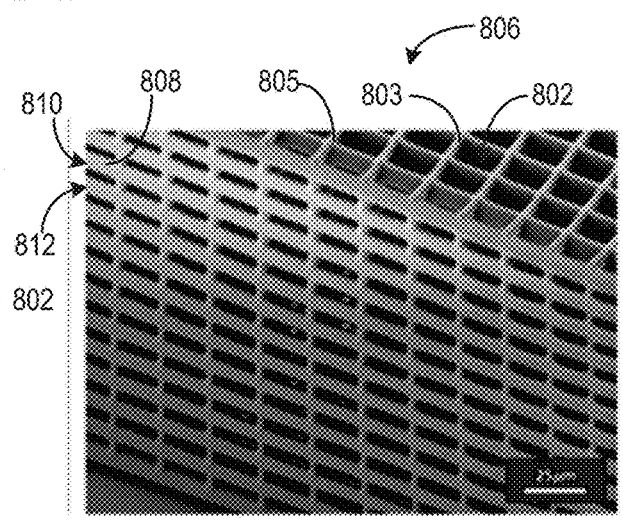
FIG. 8C is a detail view of one of the 3D printed mesh structures of FIG. 8B.

Turning now to FIGS. 8A-8C, differently scaled views of exemplary 3D structures that are configured with a relatively high surface area to footprint ratio (and/or aspect ratio) and porous or mesh-like structure are shown. FIG. 8A shows various 3D printed, mesh (or interlaced) structures 800 that can be formed via the 3D printing methods described herein. While the mesh structures 800 are shown with an overall cube shape, other geometries are possible (e.g., cuboid, ellipsoid, cone, cylinder, and the like).

As shown in the zoomed-in view of FIG. 8B (e.g., FIG. 8B can show a 40 µm scale vs. a 200 µm scale of FIG. 8A), the mesh structures 800 can be formed from alternating rows of beam, log, or cylindrical-type structures that are spaced apart from one another in a same row and that overlap and extend in cross-wise directions (e.g., the x or the y directions) in adjacent rows. For example, the mesh structures 800 can be configured as woodpile or interlaced structures with spaces 802 formed between the alternating rows of spaced-apart structures. The spaces 802 can also be referred to herein as pores or channels.

FIG. 8B shows an exemplary, first mesh structure 804 of the mesh structures 800 which has spaces 802 with a first size and an exemplary, second mesh structure 806 of the mesh structures 800 which has spaces 802 with a second size. The second size can be larger than the first size.

In some embodiments, the spaces 802 can be defined by pores 803 in an outer surface 805 of the mesh structure 800 that extend into an interior of the mesh structure 800, thereby forming a network of interconnected spaces 802 (e.g., channels) within the interior of the mesh structure 800 (FIGS. 8B and 8C). The pores 803 can also be referred to as openings or apertures.

As shown in the further zoom-in and detail view of FIG. 8C, the spaces 802 can, in some embodiments, extend from an exterior or outer surface 805 of the second mesh structure 806 (and in other embodiments, the first mesh structure 804) into an interior of the second mesh structure 806. In some embodiments, the spaces 802 can be configured as channels that extend straight through the second mesh structure 806 from one side of the structure to an opposite side of the structure.

As illustrated in FIG. 8C, in each direction (e.g., the x direction and the y direction), a spacing between the beams, logs, or cylindrical-type structures 808 in a same row (e.g., a first row 810) and a spacing between adjacent rows in the same direction (e.g., the first row 810 and a second row 812) can define a size of the spaces 802.

In this way, computer models, such as CAD models, can be used to define an overall geometry of the mesh structures 800 and a mesh or pore size of the spaces 802. Utilizing the 3D printing methods described herein, a variety of geometries for the mesh structures 800 can be produced and can be easily scaled up or down for a wide variety of applications.

Figure 9A:
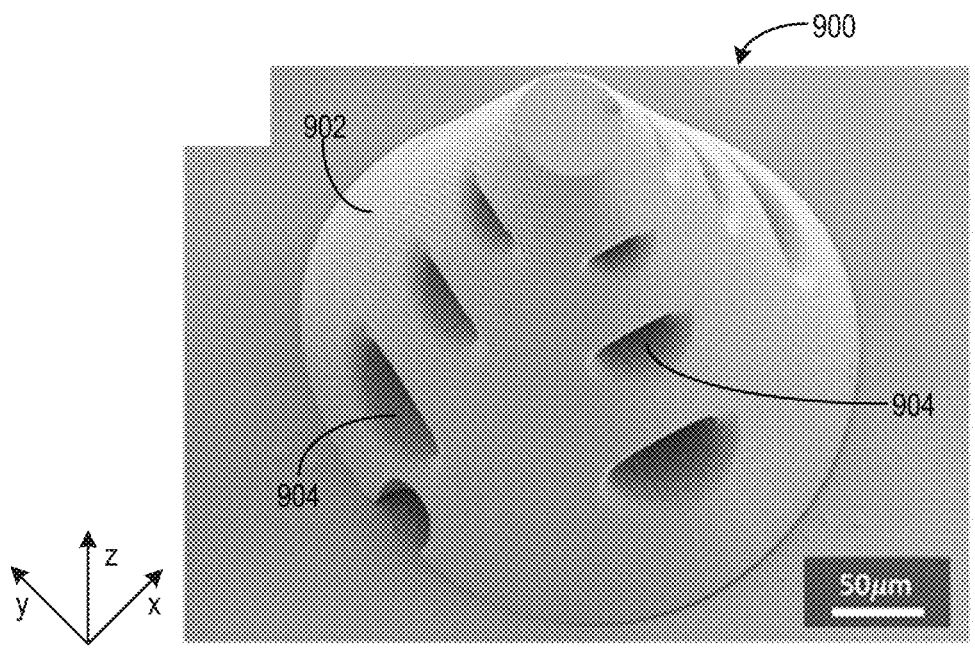
FIG. 9A is a perspective view of an exemplary conical 3D structure including one or more pores and which can be part of a 3D electronic device.
Figures 9B, 9C:
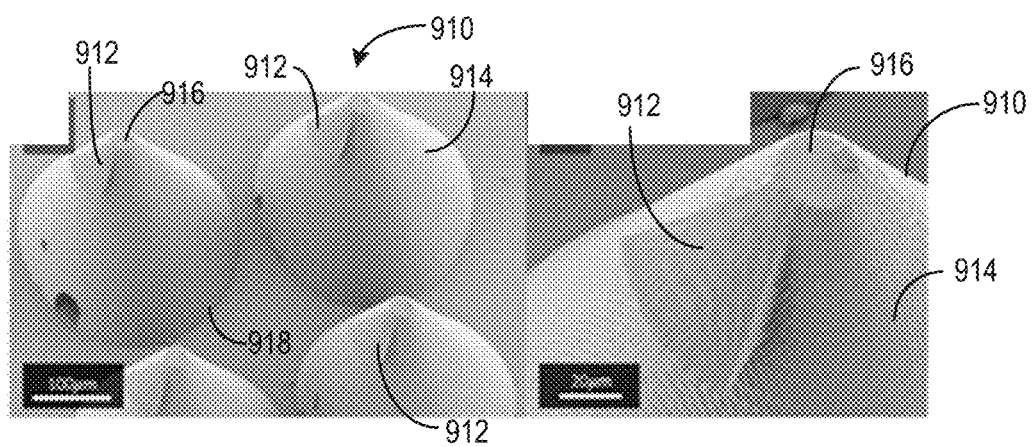
FIG. 9B is a perspective view of exemplary conical 3D structures including an extension member and which can be part of a 3D electronic device.
FIG. 9C is a detail view of one of the exemplary conical 3D structures of FIG. 9B, showing the extension member in more detail.

FIGS. 9A-9C show exemplary embodiments of 3D conical structures that are configured with a relatively high surface area (and/or aspect ratio). In some embodiments, as shown in FIG. 9A, a conical 3D structure 900 can have a conical shape with an outer surface 902 and one or more pores (or channels) 904 that extend into an interior of the conical 3D structure 900 from the outer surface 902.

In some embodiments, one or more of the pores 904 can extend into the interior of the conical 3D structure 900, only a portion of the way through the conical 3D structure (e.g., toward or to a center of the conical 3D structure 900). In other embodiments, one or more of the pores 904 can extend all the way through the interior of the conical 3D structure 900. For example, in some embodiments, one or more of the pores 904 can extend through an entirety of the conical 3D structure 900 (e.g., from one side, through the interior, and to another pore 904 disposed on an opposite side of the conical 3D structure 900). In this way, in some embodiments, an interior channel can be disposed between two pores 904 that are disposed on opposite sides of the conical 3D structure 900.

As shown in FIG. 9A, the conical 3D structure 900 includes multiple pores 904 that have a circular shape. However, in other embodiments, one or more of the pores 904 can have a different shape, such as rectangular, square, oblong, triangular, or the like.

In some embodiments, the pores 904 can be spaced apart from one another around the conical 3D structure 900. In some embodiments, each of the pores 904 can have a same size and/or geometry. In other embodiments, one or more of the pores 904 can have a different size and/or geometry from another pore of the pores 904.

A geometry (e.g., shape and size), spacing, and number of the pores 904 of the conical 3D structure can be selected based on a desired application (e.g., an intended site for implantation when used as an implantable electrode, such as the brain surface, brain ventricle, heart, or the like) and/or a desired product to be seeded within the pores 904 (as described further below). For example, such products that can be seeded within the pores 904 can include cells, growth factors, hydrogels, chemicals, drugs, or the like.

Figure 17:
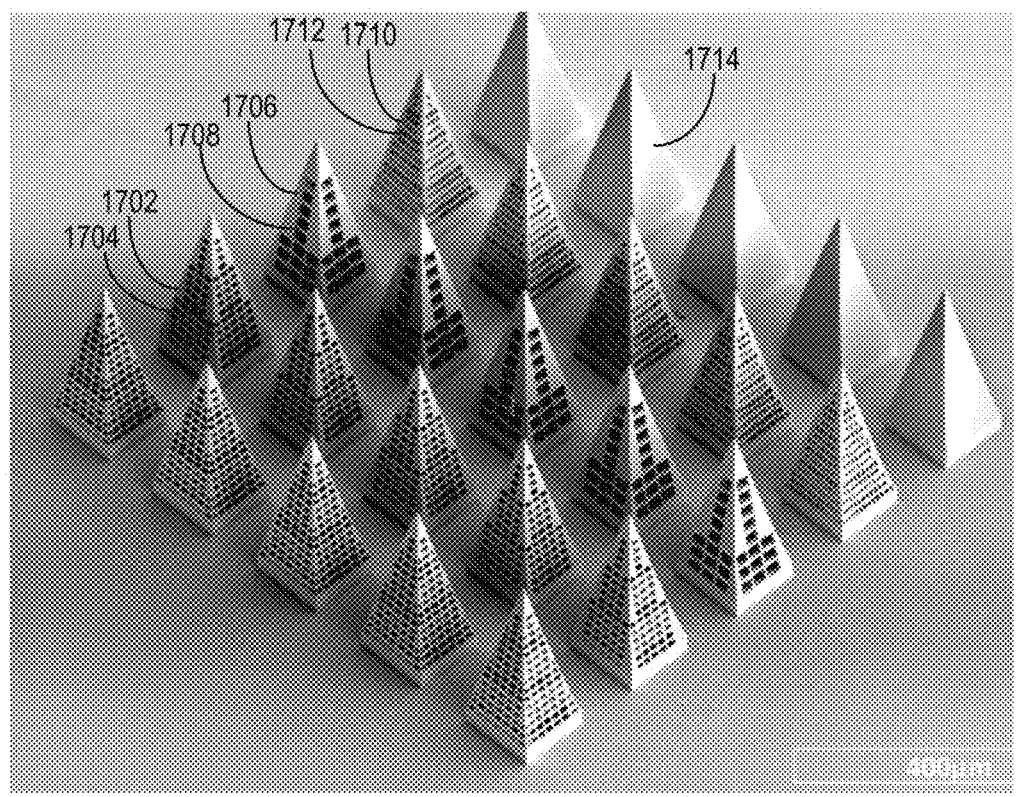
FIG. 17 is a perspective view of a plurality of pyramidal 3D structures having pores of different sizes, the structures formed by 3D printing.

In some embodiments, the pores 904 (and the other pores of the other 3D structures described herein) can have a size (e.g., aperture size) in a range of 1-900 µm, 5-400 µm, or 10-100 µm in diameter or width/height. For example, square or rectangular shaped apertures can have aperture sizes of 10 µm×10 µm, 4 µm×10 µm, 20 µm×20 µm, and the like (as shown in FIG. 17, as described further below). Pores of this scale may only be produced with high resolution 3D printers, such as the rDLW printing system described herein.

FIG. 9B and the zoomed-in, detail view of FIG. 9C show another exemplary embodiment of a conical 3D structure 910 that includes at least one 3D printed extension member 912. In some embodiments, the conical 3D structure 910 can include multiple extension members 912.

As shown in FIGS. 9B and 9C, the extension member 912 can extend outward and away from an outer surface 914 of the conical 3D structure 910. In some embodiments, the extension member 912 can have a triangular shape. However, other shapes for the extension member 912 are possible (e.g., square, rectangular, oblong, diamond, or the like).

As shown in FIGS. 9B and 9C, the extension member 912 can be disposed at or proximate to a peak 916 of the conical 3D structure 910. The extension member 912 can extend along a portion of the outer surface 914, from the peak 916 toward a base 918 of the conical 3D structure 910.

In some embodiments, the extension member 912 can be configured as a hook mechanism that is configured to decrease movement of an electrode formed from the conical 3D structure 910, when the electrode is implanted in the body for longer implantation time periods. For example, in some embodiments, the extension member 912 can be configured to grab onto, embed within, or connect to one or more tissue structures within the body, thereby holding the conical 3D electrode and/or the 3D electrode array that includes the conical 3D structure 910 in place (or reduces movement) relative to the native body tissue.

Figures 10A, 10B:
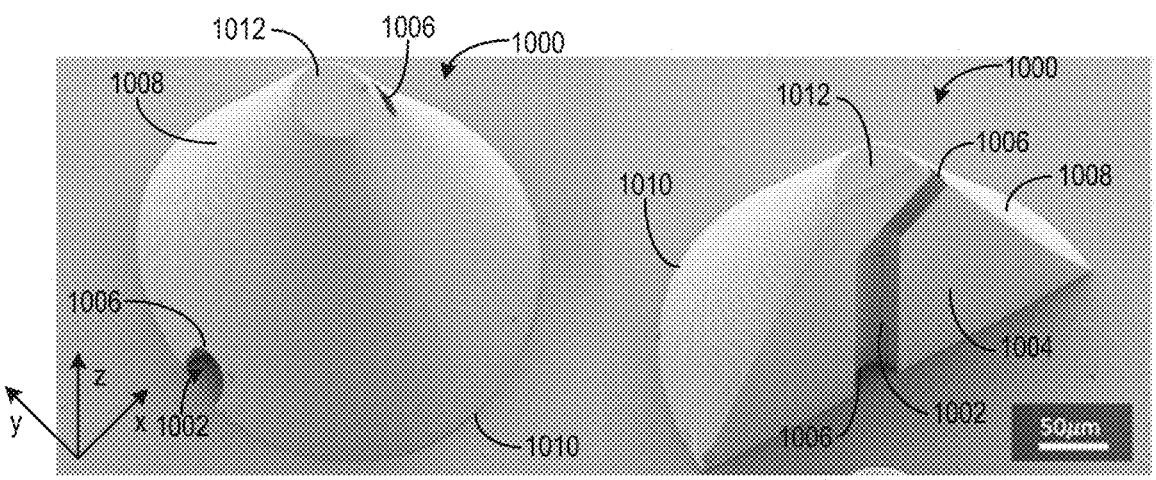
FIG. 10A is a perspective view of another exemplary conical 3D structure that has a relatively high surface area to footprint ratio and includes one or more internal channels, the exemplary conical 3D structure configured to be part of a 3D electronic device.
FIG. 10B is a cross-sectional view of the conical 3D structure of FIG. 10A.

FIGS. 10A and 10B show a perspective view and a cross-sectional perspective view, respectively, of another exemplary embodiment of a conical 3D structure 1000 that has a relatively high surface area and high surface area to footprint ratio (and/or aspect ratio). The conical 3D structure 1000 can comprise one or more internal channels 1002 that extend through an interior 1004 of the conical 3D structure 1000 (FIG. 10B).

Each channel 1002 can extend from at least one aperture (or pore) 1006 disposed on an outer surface 1008 of the conical 3D structure 1000. In some embodiments, one or more channels 1002 can extend partially through the interior 1004. In some embodiments, one or more channels 1002 can extend all the way through the interior 1004, from one aperture (or pore) 1006 to another aperture (or pore) 1006.

For example, as shown in the cross-sectional view of FIG. 10B, one channel 1002 extends from one aperture 1006 disposed at a base 1010 of the conical 3D structure 1000 to another aperture 1006 disposed proximate to (or adjacent to) a peak 1012 of the conical 3D structure 1000.

In some embodiments, the conical 3D structure can include one or more channels 1002 that extend all the way through the interior 1004 and one or more shorter channels or pores that extend only a portion of a way into the interior 1004.

In some embodiments, the one or more channels 1002 can be configured as scaffolds for electrodeposition. For example, standard electrodeposition methods can be used to form a conductive metal coating on the channels 1002 of the conical 3D structure 1000, thereby forming an electrode or other electronic component with an increased electrically conductive surface area (e.g., as compared to structures without internal channels). In some embodiments, electrodes or electrodes resulting from such electrodeposited 3D structures can be used as recording electrodes.

In some embodiments, the one or more channels 1002 can be configured as scaffolds for tissue ingrowth. For example, the one or more channels 1002 can be configured to receive one or more components therein, such as tissue growth factors, cells, drugs and the like, and/or can be configured for tissue ingrowth therein following implantation in tissue (e.g., in the body of a human or animal or in vitro).

Figure 11A:
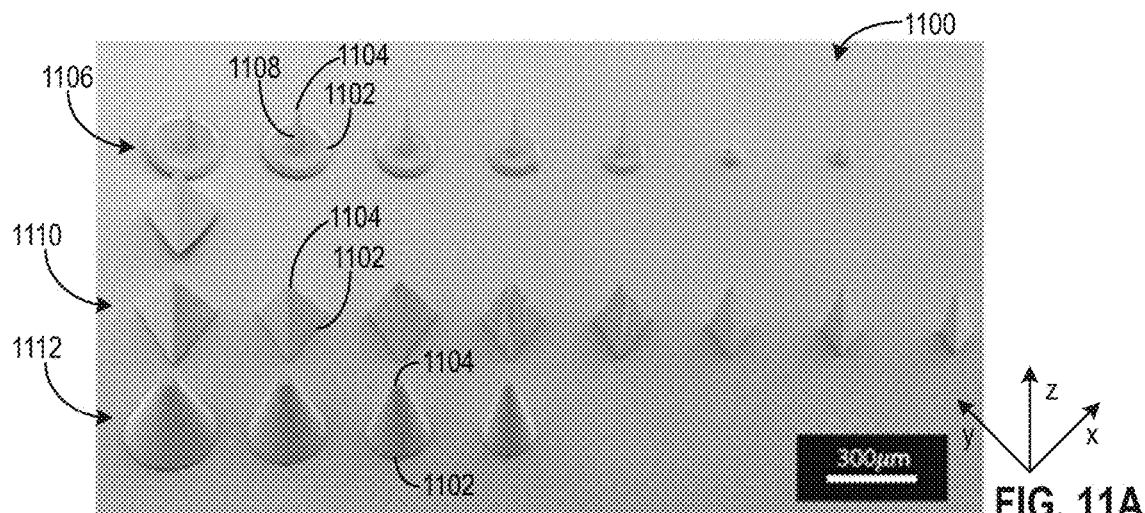
FIG. 11A shows a variety of exemplary 3D structures having a tapered or spike-shaped geometry that can be used to form 3D spike electrodes for a 3D electronic device.
Figures 11B, 11C:
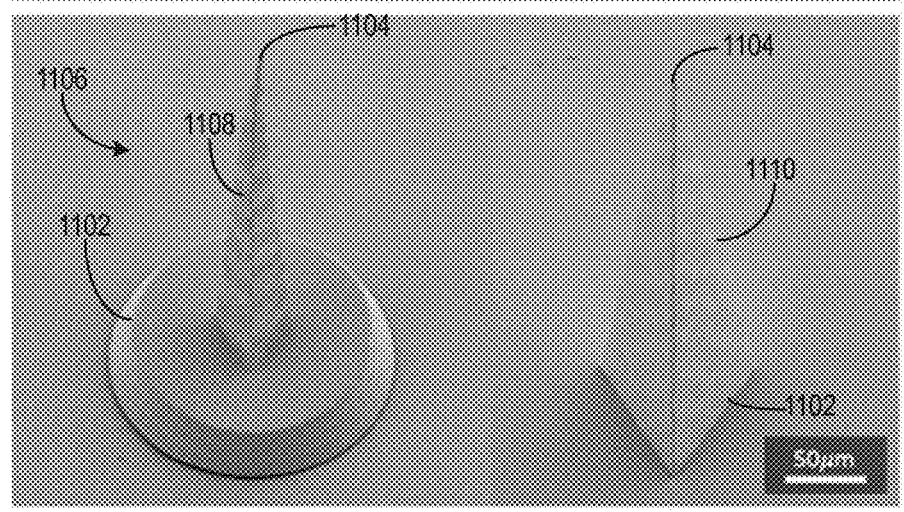
FIG. 11B is a perspective view of one of the exemplary 3D structures of FIG. 11A which has a 3D spike structure.
FIG. 11C is a perspective view of one of the exemplary 3D structures of FIG. 11A which has a pyramidal shape that tapers.

FIGS. 11A-11C show exemplary embodiments of a variety of 3D structures 1100 that can be used to form 3D spike electrodes. For example, FIG. 11A shows a variety of 3D structures 1100 having a tapered or spike-shaped geometry (or shape) that can be customized or selected from based on an intended application. In some embodiments, implantable 3D electrodes for the brain can comprise one or more of the 3D structures 1100 that are configured to penetrate past scar tissue and/or into certain regions of the brain (e.g., ventricles or other areas of the brain located beneath the tissue surface). In some embodiments, implantable 3D electrode arrays for the brain can comprise two or more differently configured 3D structures 1100 (e.g., of varying lengths, in the z direction) in order to address (e.g., stimulate) multiple brain regions of interest in one device (for example, as shown in FIGS. 14 and/or 15.

As shown in FIG. 11A, the various 3D structures 1100 can comprise a base 1102 and at least a portion that tapers from the base to a tip, point, or peak 1104 arranged away from the base 1102. The base 1102 can be configured to be disposed against the substrate of the device (e.g., the first layer printed onto the substrate). In some embodiments, when the final fabricated 3D electronic device is an implantable electrode or electrode array, the tip, point, or peak 1104 of each 3D structure 1100 can be configured to extend into (e.g., penetrate) the tissue at the implantation site. In this way, the tapered or spike-shaped geometry of the exemplary 3D structures 1100 can be configured to penetrate through scar tissue to reach desired neurological tissue for stimulation and/or recording.

As shown in FIG. 11A, a first set of 3D structures 1106 can be configured as spike electrodes with a 3D spike structure 1108 extending from the base 1102. The spike structure 1108 can narrow from the base 1102 to the peak 1104, which can be pointed. A second set of 3D structures 1110 can have a pyramidal shape that tapers from the base 1102 to the peak 1104. A third set of 3D structures 1112 can have a conical shape that tapers from the base 1102 to the peak 1104 (e.g., similar to the conical 3D structures shown in FIGS. 9A-10B).

In FIG. 11A, an aspect ratio of each set of 3D structures (e.g., the first set 1106, the second set 1110, and the third set 1112) increases from the left to the right side of the page. This aspect ratio can be defined between a distance between (in the z direction) the base 1102 and the peak 1104 (e.g., a height or length of the 3D structure 1100) and a diameter or width of the base 1102. As such, as the aspect ratio of the 3D structure 1100 increases, the 3D structure 1100 can become more narrowed or pointed, thereby enabling better (and in some embodiments, deeper) penetration into a target tissue or alternate structure.

FIG. 11B shows one of the first set of 3D structures 1106 in more detail. FIG. 11C shows one of the second set of 3D structures 1110, which has a higher aspect ratio, in more detail.

Turning now to FIG. 17, a plurality of pyramidal 3D structures having pores of different sizes are shown. For example, FIG. 17 shows two rows of a first pyramidal 3D structure 1702 comprising spaced apart pores 1704 with a pore (or aperture) size of 10 µm×10 µm one row of a second pyramidal 3D structure 1706 comprising spaced apart pores 1708 with a pore size of 20 µm×20 µm, one row of a third pyramidal 3D structure 1710 comprising spaced apart pores 1712 with a pore size of 4 µm×10 µm and one row of a fourth pyramidal 3D structure 1714 that is solid and without pores. As described above, utilizing the 3D printing methods described herein, pore sizes from around 1 µm to hundreds of µm in diameter (or square) can be created on the 3D structures for the 3D electrodes. In this way, by utilizing the 3D printing and photolithography methods described herein, 3D electrodes with a customized (e.g., selected for a particular application and/or to receive a certain active material) pore size and/or arrangement can be easily and quickly fabricated.

Figure 18:
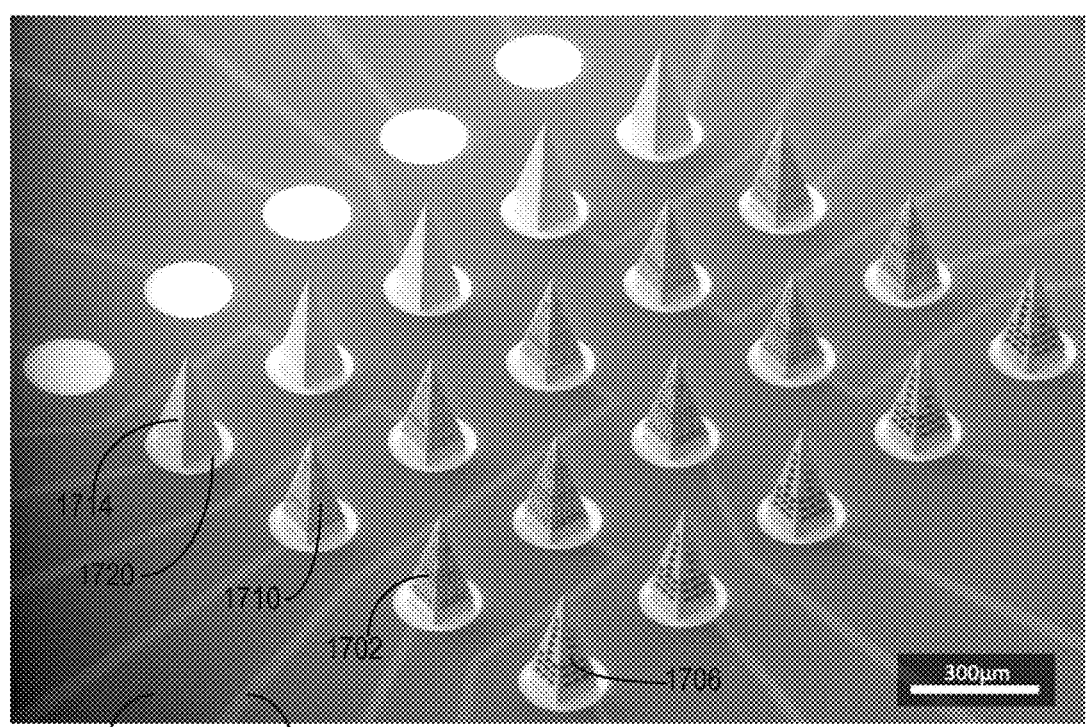
FIG. 18 is perspective view of a portion of an insulated substrate comprising a plurality of electrical traces connected to corresponding print pads and the various pyramidal 3D structures of FIG. 18 printed onto the print pads.
Figure 19:
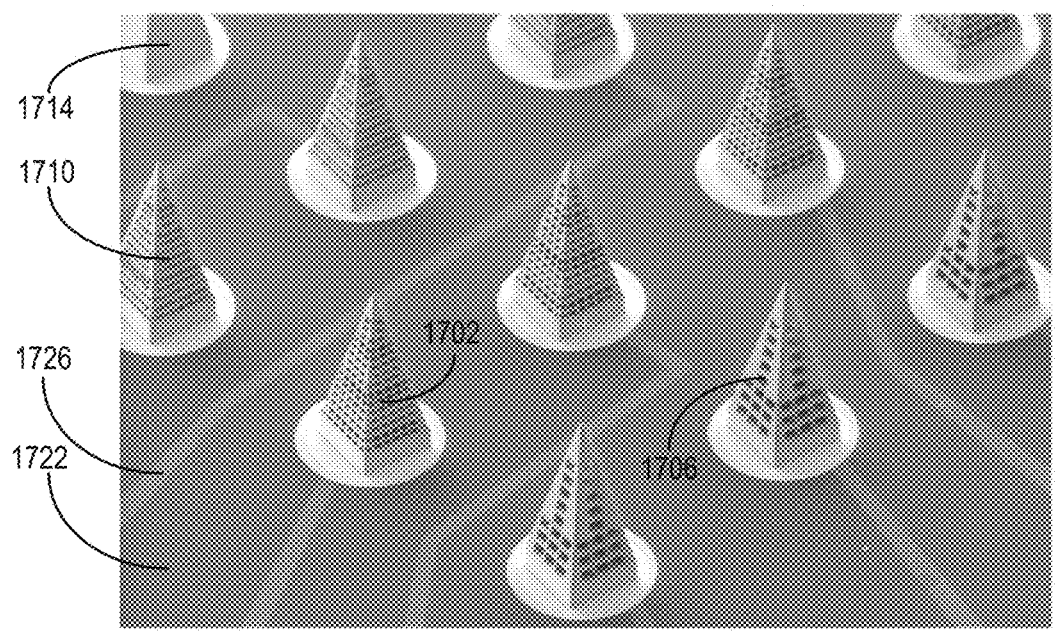
FIG. 19 is a zoomed-in view of a portion of the view of FIG. 18, illustrating the pore structures of the pyramidal 3D structures in more detail.

For example, as shown in FIG. 18 and FIG. 19 (which is a zoomed-in view of a portion of FIG. 18), the various pyramidal 3D structures shown in FIG. 17 can be printed onto print pads 1720 of a substrate 1722 comprising a plurality of electrical traces 1724 (which may be covered by an insulating layer over the traces and the substrate) and then metallized to form a 3D multielectrode array.

As introduced above, a geometry of the 3D structures 1100 shown in FIGS. 11A-11C can be customized and specified base on an intended application and/or implantation site. By utilizing the 3D printing methods disclosed herein, computer models can be quickly and easily updated to reflect the specified geometry for the 3D structure and then printed on the substrate and fabricated into a 3D electronic device.

For example, the specific geometric features of the 3D structures described above with reference to FIGS. 8A-11C may only be achievable via the 3D printing platform described herein. For example, the high surface area to footprint ratio and/or aspect ratio, pores, internal channels, extension members for reduced movement, and tapered or spiked shapes of the 3D structures can be fabricated easily and efficiently by utilizing a 3D printer (and, in particular, a rDLW printer). Such 3D structures for use as metallized, 3D electrodes may not be fabricated by other methods. For example, utilizing photolithography techniques alone may produce a few layers of patterned material on a flat substrate. However, attempting to make more 3D structures with higher aspect ratios (e.g., in the z to x or y directions) using photolithography techniques may be time consuming and costly. Additionally, the intricate geometric features of the 3D structures described herein may only be able to be produced using the rDLW printing system that can print with high resolution on a micron scale. Further still, in some embodiments metalizing 3D printed porous structures, as described above, may only be possible using the techniques described herein (e.g., the metallization methods described above with reference to FIGS. 7, 12, 28, and 29 which utilize a sacrificial metal layer). For example, other metallization techniques may result in clogged pores of the 3D structure, thereby decreasing the surface area and tissue ingrowth potential of the 3D electrode array.

Additionally, only the 3D printing methods described here can provide high resolution printing capable of producing a high density multielectrode array. In particular, alternate 3D printing methods, such as printing using an aerosol jet 3D printer, cannot achieve the higher resolution printing of the two photon lithography printing method described herein. As an example, the printing methods used herein can print on the micron scale (e.g., single micrometer) vs. alternate 3D printing methods (e.g., 10-20 μm resolution with aerosol jet 3D printing).

For example, any of the multielectrode arrays described herein can have a pitch or spacing between 3D electrodes of approximately 90 μm (e.g., ±3 μm) or in a range of 30-500 μm, 30-100 μm, 80-100 μm, 85-95 μm, 70-200 μm, or 200-500 μm. The DLW two-photon 3D printing methods described herein can be capable of producing multielectrode arrays with a spacing or pitch between 3D electrodes of anywhere from 40 μm up to 9 mm.

In this way, 3D printing 3D structures onto substrates and selectively metallizing those 3D structures, as described above, can form 3D electronic devices with a relatively high surface area, surface area to footprint ratio, and/or aspect ratio, and with a relatively densely packed array of 3D electrodes. As such, these 3D electronic devices can have increased capacity for sending and receiving electrical signals while also having a smaller overall footprint. Further, these 3D electronic arrays can comprise 3D electrodes capable of penetrating tissue, thereby decreasing an immune response to the device and improving anchoring and/or ingrowth at the tissue. As a result, a longevity and long-term applicability of these devices can be increased.

By fabricating thin film electrodes or electrode arrays with 3D electrodes that have a higher surface area, surface area to footprint ratio, and/or aspect ratio, such as the metallized 3D structures described herein, 3D electrodes or 3D multielectrode arrays comprising 3D printed electrodes (which can comprise a photopolymer coated in metal) can be formed that can be used for both short and long-term applications in the body.

For example, by increasing the electrochemical surface area of the electrode or electrode array (e.g., by utilizing one of the 3D structures described herein with reference to FIGS. 8A-11C), the resulting 3D electrode or electrode array can more effectively stimulate the brain. For example, an ability of an electrode or electrode array to stimulate the brain can be directly related to the surface area of the electrode or electrodes of the array. For example, fabricating thin film electrodes or electrode arrays with 3D electrodes that are porous can increase the electrodes' available surface area for electrostimulation, while at the same time promoting tissue ingrowth into the pores.

Figure 20:
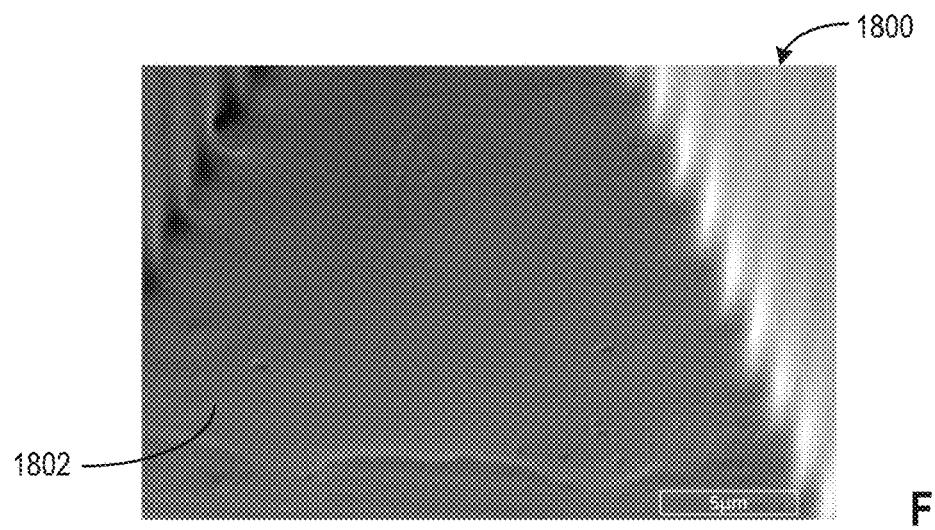
FIG. 20 is an exemplary microscopic image of a surface of a 3D printed 3D structure, directly after printing and prior to applying a surface treatment to create a more roughened surface.

In some embodiments, to further increase the available surface area for electrostimulation in a 3D stimulation electrode (which can be part of a multielectrode array) or another type of 3D electrode, a micro surface area of the 3D electrode can be increased by roughening the surface (exposed outer surface) of the 3D electrode. For example, various surface treatments can be applied to the 3D electrodes and electrode structures described herein to create a roughened surface (on the micro scale). FIG. 20 shows an exemplary microscopic image 1800 (scanning electron microscope image) of a (outer) surface 1802 of a 3D printed 3D structure, directly after printing and prior to applying a surface treatment to create a more roughened surface. As shown in the image 1800, the surface 1802 is relatively smooth and any non-smooth portions of the surface 1802 (if present) are artifacts of the printing process. In some embodiments, the 3D printed 3D structure can be one of a plurality of 3D structures printed onto a prepared substrate of a 3D multielectrode array, as described above.

Figure 21:
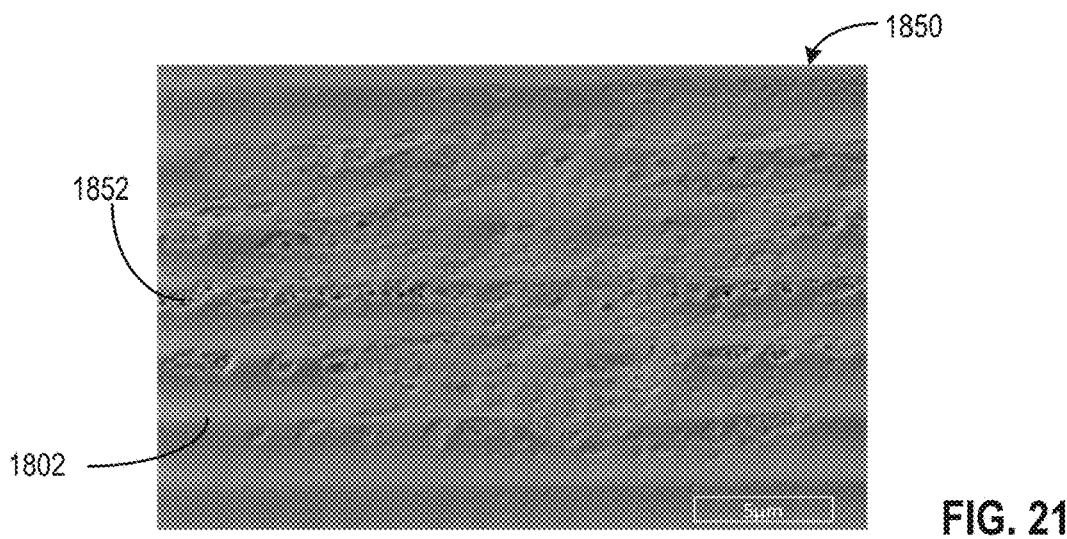
FIG. 21 is an exemplary microscopic image of the surface of the 3D printed 3D structure of FIG. 21, after exposing the surface to oxygen plasma to create a roughened surface.

As one embodiment, a plasma treatment can be applied to a 3D printed structure, prior to metallizing, which etches the surface of the 3D structure and creates a surface roughness. For example, devices including one or more 3D printed structures can be roughened via exposure to an oxygen plasma to increase the surface roughness, and thus, the surface area. FIG. 21 is an exemplary microscopic image 1850 (scanning electron microscope image) of the surface 1802 of the 3D printed 3D structure, which now has a surface roughness 1852 due to 10 minutes of exposure to 100 W oxygen plasma. The surface roughened 3D structure(s) can then be metallized following the methods described herein with reference to FIGS. 3 and 12 (e.g., the plasma treatment can be applied at 1214, prior to the metallization method at 1216 in FIGS. 12A and 12B).

As another embodiment, iridium oxide could be applied (e.g., electrodeposited) to the metallized 3D printed structures (e.g., on top of the sputtered metal at 1216 or 1218 of the method shown in FIGS. 12A and 12B) to create a micro-scale surface roughness and/or increased thickness on the 3D electrodes, similar to that shown in FIG. 21. This iridium oxide application may be used in conjunction with the methods described below with reference to FIGS. 22-27.

In some embodiments, both the plasma treatment and the iridium oxide treatment can be applied to the 3D structures (pre and post metallization, respectively, as described above) to create different or a greater roughening effect on the surface of the metallized 3D printed electrodes.

In some embodiments, by fabricating thin film electrodes or electrode arrays with 3D electrodes that have a tapered or spike-shaped structure (e.g., as shown in FIGS. 11A-11C), the 3D electrodes can penetrate through scar tissue and reach a desired brain tissue for stimulation and/or recording.

Thus, by selectively metallizing 3D structures that are 3D printed onto a substrate (e.g., using method 300 of FIG. 3) a variety of 3D electronic devices can be fabricated, such as complex, high surface area stimulation electrodes, high density neural recording electrodes, and 3D scaffold electrodes.

As introduced above, the 3D electronic devices described herein can be used for various applications. One such application includes implantable 3D electrodes (a multielectrode array comprising multiple 3D electrodes) for neurostimulation and/or recording in the body (e.g., in the heart, spinal cord, brain surface, brain ventricles, and the like). In some embodiments, implantable 3D electrodes and 3D multielectrode arrays can be implanted in the brain and used for neural stimulation and/or recording. In some embodiments, the implantable 3D electrodes or multielectrode arrays can be implanted in the brain for longer-term applications, such as deep brain therapy for chronic neurological conditions (e.g., Parkinson's disease, dystonia, and essential tremor).

As an example, 3D multielectrode arrays formed using the methods described herein and comprising selectively metallized 3D printed structures (3D electrodes) can be configured as high surface area 3D scaffold multielectrode arrays that enhance neural stimulation when implanted in a portion of the nervous system of the body (e.g., the brain). As introduced above, a higher electrode surface area, which can be achieved with a 3D printed 3D structure comprising a plurality of pores (e.g., as shown in FIGS. 8A-11C), can result in a device with increased surface area for electrical stimulation, thereby making the devices more effective without requiring a large device (substrate) footprint. Thus, smaller devices can achieve increased levels of electrostimulation. Additionally, 3D electrode arrays comprising 3D electrodes having a plurality of pores can promote tissue ingrowth into the pores of the electrodes, thereby increasing a longevity of the arrays. More specifically, by integrating pores or channels within the 3D printed structures of the 3D electrodes, enhanced tissue integration with the implanted 3D electrode or multielectrode array can be achieved. This tissue integration can reduce thresholds for stimulation and increase a longevity of the device when implanted (e.g., the 3D electrodes or electrode arrays can be implanted for a longer period of time while maintaining their stimulation and/or recording capabilities).

Further, in some embodiments, the porous or internal channel structure of the 3D electrodes of the multielectrode arrays can serve as scaffolds that are configured to receive various growth factors, such as vascular growth factors or neurotrophic factors which promote cell ingrowth with tunable selectively. For example, 3D electrodes formed from 3D printed structures comprising pores or internal channels (e.g., as shown in FIGS. 8A-8C, 9A, 10A, and 10B) can be seeded with neurotrophic factors and/filled with a hydrogel containing active materials (e.g., growth factors) and then implanted in the body. The growth factors (e.g., neurotrophic factors) can promote cell ingrowth from the native tissue at the implantation site into an interior of the 3D electrode(s) of the implanted device, thereby increasing a long-term stability of the implanted device. As a result, the implanted 3D electrode or multielectrode array can be used more effectively for a longer period of time (as compared to flatter electrodes or electrode arrays that do not include 3D electrodes formed from 3D printed structures comprising pores or internal channels, such as the exemplary planar electrode array 10 shown in FIG. 1A and array 50 shown in FIG. 1B).

In some embodiments, the specific growth factors or neurotrophic factors to be used within a 3D electrode or electrode array can be selected based on an intended implantation site and/or application. For example, the selection of the specific neurotrophic factors can induce the incorporation of inhibitory or excitatory neurons within the 3D electrode or electrode array.

Thus, 3D neurostimulation electrodes comprising selectively metallized 3D printed structures can have lower power consumption, an increased implantation lifetime, and a smaller footprint. Such 3D neurostimulation electrodes can be effective for a variety of applications, including (but not limited to) deep brain stimulation, close-loop feedback of neuromodulation, retinal implants, and the like.

Further, 3D recording electrodes comprising selectively metallized 3D printed structures can have long-term recording capabilities due to the features described above. For example, enhanced tissue integration of the implanted device with the native tissue at the implantation site, due to the specific geometries of the 3D printed electrodes described herein that allow for the incorporation and delivery of neurotrophic factors, can enhance the long-term performance of the 3D recording electrodes or multielectrode array. Additionally, by incorporating extension members (e.g., hooks) into the 3D printed structures of the 3D electrodes, the resulting device can be better anchored within the tissue at the implantation site. This can minimize any damage to the tissue at the implantation site that can be associated with electrode movement. By reducing movement between the 3D recording electrode and the native tissue, more effective and long-term recording (and stimulation for stimulation electrodes) can be accomplished, even when the subject is in motion.

As another example, 3D printed structures with higher aspect ratios and/or surface area to footprint ratios (such as an aspect ratio of at least 10:1) can penetrate the tissue where they are implanted, thereby reducing an immune response and providing better anchoring to the tissue, as well as being able to address deeper regions in the tissue. For example, FIGS. 23 and 30A-31 show examples of shank or spike-shaped structures for 3D electrodes that can have high aspect ratios. In some examples, these 3D structures, formed using the 3D printing methods described herein) can have a height in a range or 300-400 µm and a width (or diameter) or approximately 20 µm. In some examples, a base of the 3D structure can be approximately 40 µm and a tip of the 3D structure can be approximately 20 µm. In some examples, the 3D structures can have a height in a range of 150-400 µm with a sharper tip (such as those shown in FIGS. 30A-31, as described below). As such, the spike, conical, or shank-shaped electrodes described herein can be configured to penetrating the dura (of the brain or spinal cord) and be used in neural implants. For example, if the spike, conical, or shank-shaped 3D electrode was wider or shorter than described above, it may be unable to penetrate the dura.

Figure 22:
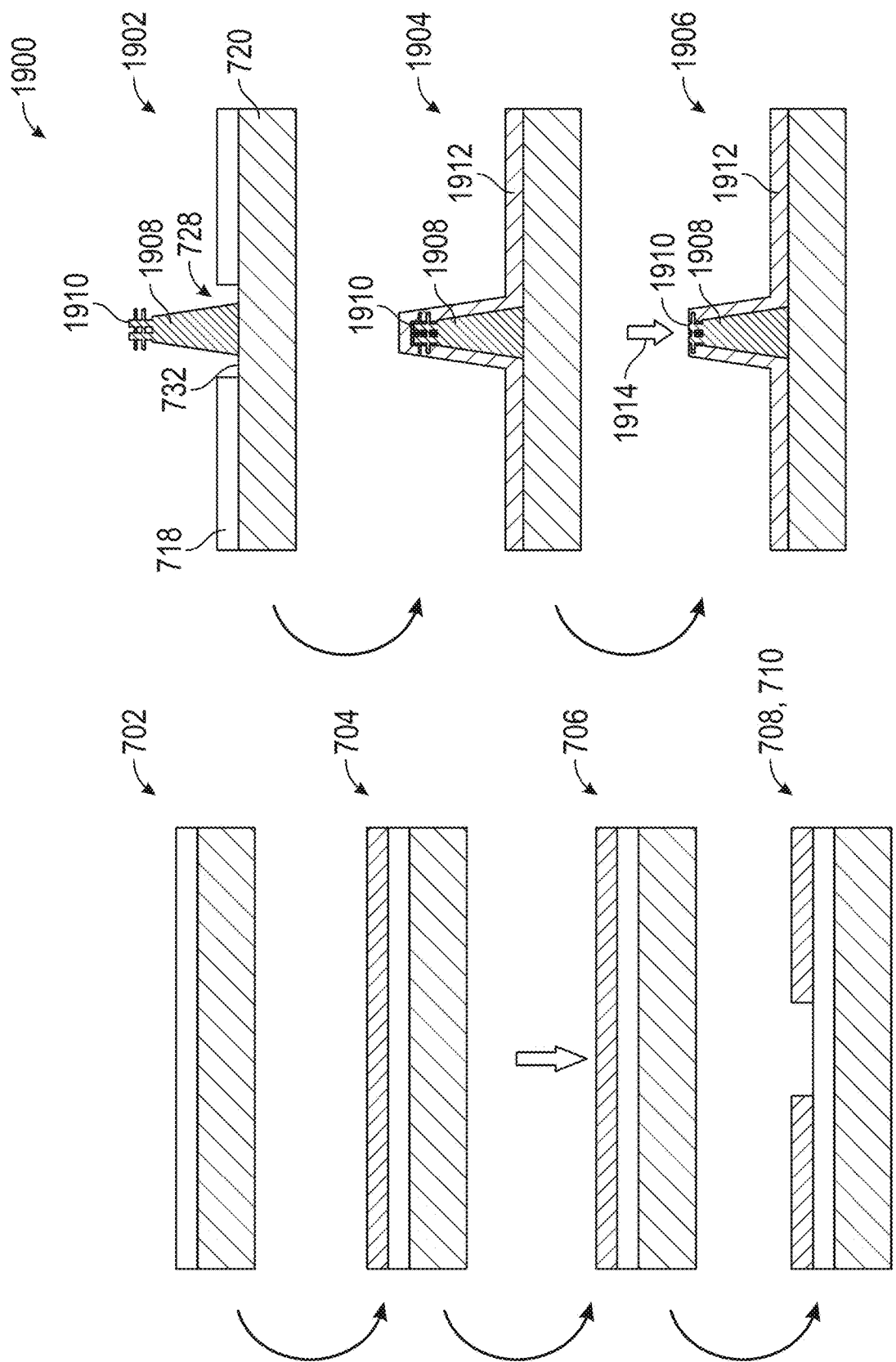
FIG. 22 is an exemplary method for creating insulated recording or stimulation electrodes with an exposed metal tip for recording or stimulation.

In some embodiments, 3D recording or stimulation electrodes can be further insulated for recording or stimulation applications by applying an insulating material coating (such as Parylene C or amorphous Silicon Carbide (a-SiC)) on top of the metal surface of the 3D structure of the 3D electrode (e.g., following metallization of the 3D printed structure) and then exposing (by removing the insulating or Parylene or a-SiC coating from) only a metal tip (apex) of the 3D structure for electrical recording or stimulation. An exemplary method 1900 for creating insulated recording or stimulation electrodes with an exposed metal tip (for recording or stimulation) is shown in FIG. 22. Method 1900 follows a similar method as shown in FIG. 7. Thus, similar methods to those of FIG. 7 are labeled similarly in FIG. 22 and are not re-described below for the sake of brevity.

After creating the opening 728 in the sacrificial metal layer 718 to the underlying substrate 720 to expose a selected portion or exposed portion (e.g., print pad) 732 of the substrate 720 (as described above with reference to FIG. 7), the method continues on to 1902. At 1902, the method includes 3D printing a 3D structure 1908 onto the exposed portion 732 of the substrate 720. The 3D structure 1908 can have a conical, pyramidal, or spike (or shank) shape with a mesh (or logpile or porous) structured tip 1910 (e.g., the highly porous or mesh structure is added to an end or tip of the conical, pyramidal, or spike 3D structure 1908, thereby creating a tip 1910 with pores or channels and increased surface area). Alternatively, the 3D structure 1908 can have a conical, spike, or shank with a tapered tip that does not include a mesh structure.

The method at or following 1902 can then include applying a metal layer to the device with the 3D structure 1908 having the tip 1910 and then removing the sacrificial metal layer, as described above with reference to the methods at 714 and 716 of method 700 of FIG. 7.

The method 1900 then continues to 1904 where Parylene (Parylene C) or amorphous Silicon Carbide (a-SiC) (or another insulating material) is deposited across the device to create an insulating layer 1912 (of Parylene C or a-SiC, for example) over the metallized 3D structure 1908 and tip 1910. In some embodiments, a thickness of the insulating layer 1912 can be approximately 2 µm. This insulating layer 1912 electrically isolates both the electrical leads (traces) and the device itself from the environment.

In some embodiments, the method at 1904 can further include, prior to depositing the insulating material of the insulating layer 1912, electrodepositing iridium oxide (or a similar material such as platinum black or PEDOT) across the device to create increased surface roughness and/or increase the thickness of the metal on the device. The insulating material can then be deposited, as described above. Alternatively, in other instances, electrodepositing the iridium oxide material can be performed after the method at 1906 (as described below), thereby adding surface roughness and/or increased thickness to only the exposed metal tips of the 3D structures (electrodes).

At 1906, the method includes removing the insulating layer 1912 from only the tip 1910 of the 3D structure 1908 by exposing the portion of the insulating layer 1912 covering the tip 1910 to a laser (e.g., a 40 W femtosecond pulsed laser having micron resolution). As shown at 1906 in FIG. 22, this results in the exposure of the conductive metal at the tip 1910 for electrical recording or stimulation, while a remainder of the 3D structure 1908 (not at the tip) and the device remain covered by the insulating layer 1912 (and thus isolated from the environment).

Figure 23:
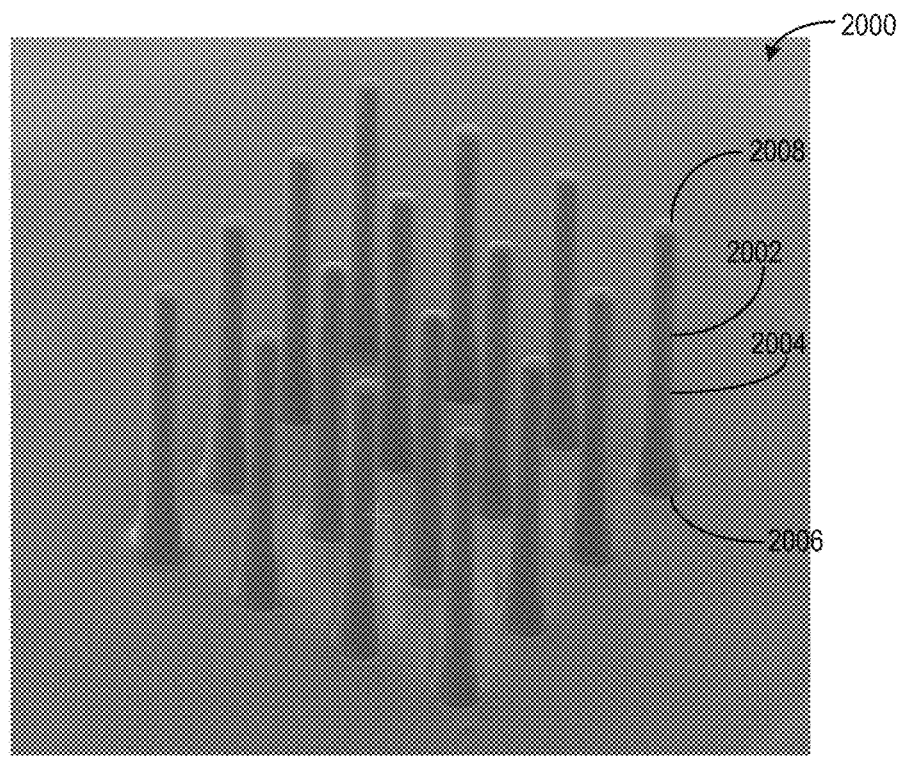
FIG. 23 is an exemplary device (e.g., multielectrode array) comprising a plurality of shank or spike-shaped 3D printed electrodes which are covered in an insulating layer (prior to uncovering the metallized tip).

In some embodiments the 3D structure 1908 for recording or stimulation electrodes can have a conical, spike, or shank-like 3D structure. An exemplary device (e.g., multielectrode array) 2000 comprising a plurality of shank or spike-shaped 3D printed electrodes 2002 which are covered in a Parylene layer 2004 (or another insulating material, such as a-SiC) (prior to uncovering the metallized tip) is shown in FIG. 23. Each spike-shaped 3D printed electrode 2002 has a 45 µm base 2006, a 20 µm tip 2008, and is 340 µm in height (in the z-direction). It should be noted that the configuration of the device 2000 is exemplary and other shapes and sizes for the 3D printed electrodes 2002 are possible with the 3D printing techniques described herein.

Figure 24:
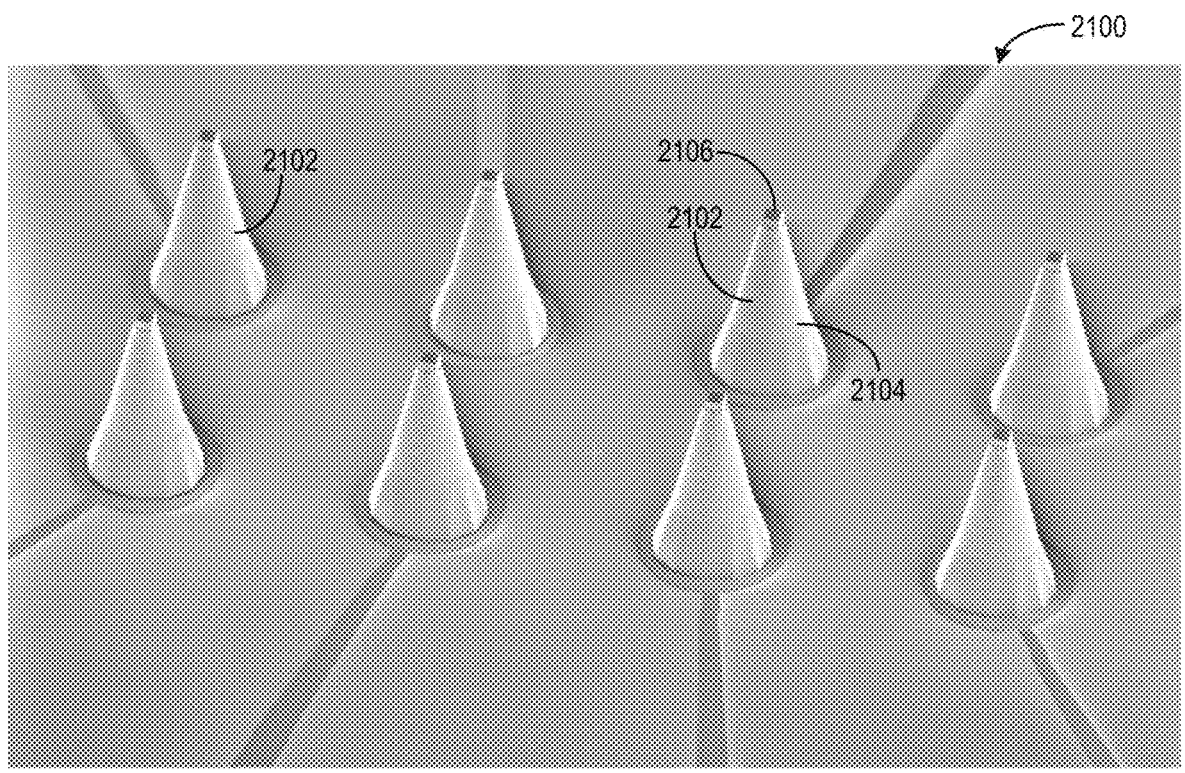
FIG. 24 is another exemplary device (e.g., multielectrode array) comprising a plurality of conical-shaped 3D printed electrodes which are covered in an insulating material, except for an exposed, metallized and mesh-structure (porous) tip.

Another exemplary device 2100 that can be created with the method 1900 presented at FIG. 22 is shown in FIG. 24. The device 2100 comprises a plurality of 3D printed electrodes 2102 having a conical shape and covered in Parylene 2104 (or another insulating material, such as a-SiC), except for an exposed, metallized and mesh-structure (porous) tip 2106. The tip 2106 comprises conductive metal and is porous, thereby providing a high surface area tip for recording and stimulation while a remainder of the device 2100 is insulated. In some embodiments, as shown in FIG. 24, the tip 2106 comprises pores while a remainder of the 3D structure of the 3D printed electrode 2102 is solid (e.g., not having pores).

FIGS. 25-27 show exemplary microscopic images of the tip 2106 of one 3D printed electrode 2102 of device 2100 before removing the Parylene 2104 from the tip 2106 (FIG. 25) and after removing the Parylene 2104 from the tip 2106 (FIGS. 26 and 27) to expose a conductive metal surface 2110 of the tip 2106. As shown in FIG. 27, the tip 2106 has an increased surface area for electrical recording or stimulation due to its network of channels or pores 2112.

Additional exemplary methods 2200 and 2250 for creating multielectrode arrays with a plurality of insulated recording or stimulation 3D electrodes with an exposed metal tip (for recording or stimulation) are shown in FIGS. 28 and 29. Methods 2200 and 2250 follow a similar method as shown in FIGS. 7 and 22. Thus, similar methods to those of FIGS. 7 and 22 are labeled similarly in FIGS. 28 and 29 and are not re-described below for the sake of brevity.

The methods 2200 and 2250 both include, at 702, applying a sacrificial metal layer 718 (e.g., via sputtering) onto a surface of a substrate 2202 (FIG. 28) or substrate 2252 (FIG. 29). In some embodiments, the sacrificial metal layer 718 can comprise chromium. Further, the sacrificial metal layer 718 can serve as a sacrificial mask layer. The substrate 2202 can include a silicon wafer or another substrate described herein (FIG. 28), which may be covered by polyimide in some instances. The substrate 2252 can include a silicon wafer 2254 (or other base substrate) that is covered by a polyimide layer 2256 (or another thin film material layer) (FIG. 29). For example, in the method 2250, prior to the sputtering the sacrificial metal layer 718 onto the substrate 2252, polyimide can be spun onto the surface of the silicon wafer 2254, as shown at 2251 (FIG. 29). In some examples, the method at 2251 can additionally include adding an adhesion promoter to an edge of the silicon wafer 2254 prior to adding the polyimide layer 2256.

Then, at 704, a positive photoresist 722 is spun onto the surface of the sacrificial metal layer 718, thereby covering the sacrificial metal layer 718 (FIGS. 28 and 29). The methods 2200 and 2250 then include, at 706 and 708, photopatterning openings in the positive photoresist 722, thereby defining spaces for the electrical contacts and traces of the multielectrode array. For example, the methods can include patterning the positive photoresist 722 using a mask aligner (and direct write laser lithography system). After the positive photoresist 722 is exposed to a developer solution, the methods continue to 710 to etch through the sacrificial metal layer 718, thereby forming the mask (or spaces) for the final electrical traces and contacts and defining print pads 2260 on the substrate 2202 (FIG. 28) or the polyimide layer 2256 (FIG. 29).

Figure 30A:
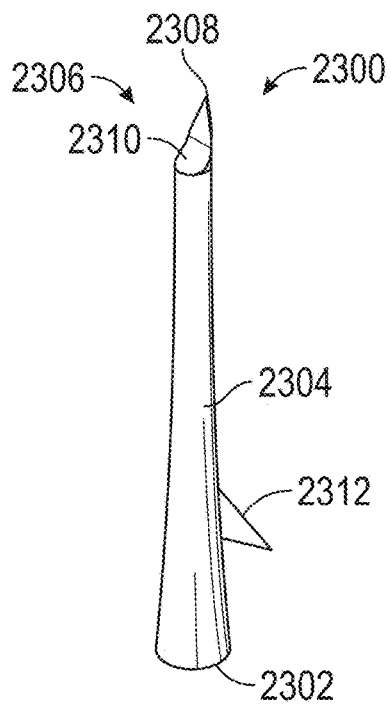
FIG. 30A is a perspective view of an exemplary spike-shaped structure for a 3D electrode, where a tip of the structure has a mosquito proboscis-like shape.
Figure 30B:
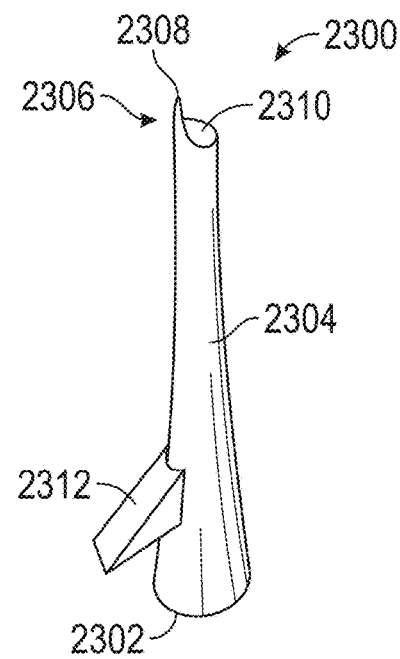
FIG. 30B is another perspective view of the 3D electrode structure of FIG. 30A.
Figure 31:
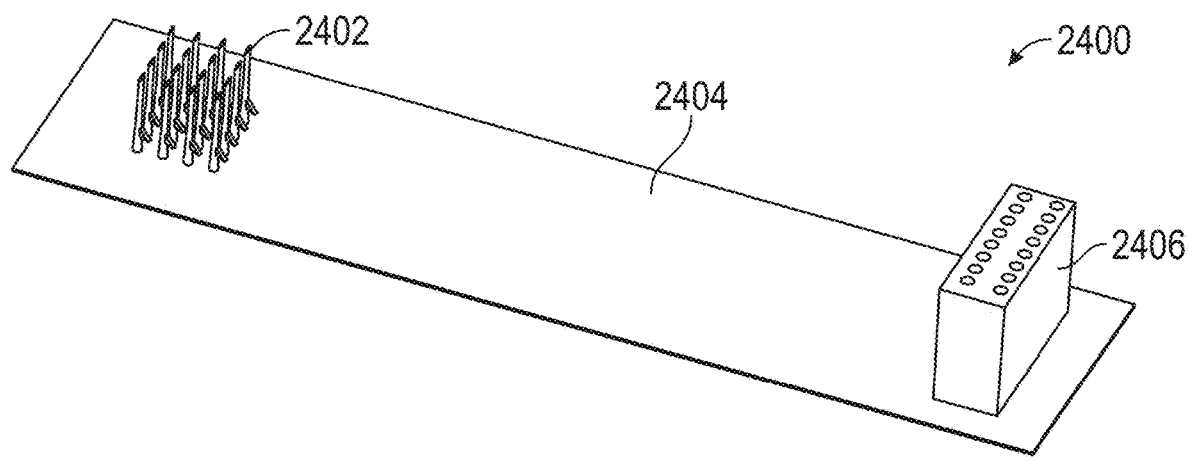
FIG. 31 is a perspective view of an exemplary 3D multielectrode array comprising a plurality of 3D spike electrodes disposed on a thin-film substrate.

The methods 2200 and 2250 then continue to 2262 (which can be similar to methods 712, 1902, and 1214 described above) to print a 3D structure 2264 onto each of the print pads 2260 (FIGS. 28 and 29). As described herein, in some examples, each 3D printed structure can have an aspect ratio of at least 10:1 and comprise a photopolymer. In other examples, each 3D printed structure can have an aspect ratio of at least 3:1 or 7:1. Additional examples of such 3D printed structures are shown in FIGS. 30A-31, as described further below. In still other examples, each 3D printed structure can comprise a photopolymer and a plurality of pores.

At 2266, the methods include sputtering the entire sample surface, including the 3D structures 2264, the openings (or windows) for the electrical contacts and traces, and a remaining portion of the sacrificial metal layer 718, with metal to form a top metal layer 2268 (FIGS. 28 and 29). The top metal layer 2268 can comprise one or more metals, such as platinum, titanium, gold, or a combination thereof (e.g., platinum and titanium). The sacrificial metal layer 718 is then lifted off at 2270 (FIGS. 28 and 29), for example by using an etchant, thereby revealing metallized 3D printed structures 2272 that are in direct electrical contact with metallized electrical traces 2274 and electrical contacts 2276.

The methods 2200 and 2250 can then include, at 2278, coating the entire device with an insulating material (e.g., Parylene C or a-SiC), thereby creating an insulating layer 2280 over the device (FIGS. 28 and 29). At 2282, the methods 2200 and 2250 include removing the insulating layer 2280 from only the tips of the metallized 3D printed structures 2272 (e.g., by laser ablation, as described above), thereby exposing metallized tips 2284 of the metallized 3D printed structures 2272 while a remainder of the device remains coated with the insulating layer 2280. The final device shown in FIG. 28 is a 3D multielectrode array comprising a plurality of 3D electrodes that are insulated with only exposed metallized, conducting tips for recording and/or stimulation applications. Thus, the electrical traces of the multielectrode array are isolated from each other and the environment, while the metallized conducting tip of the 3D electrodes are exposed to the environment.

The method 2250 can further continue to 2286 to release the full device (multielectrode array) from the silicon wafer 2254 (e.g., using a laser), thereby resulting in the 3D multielectrode array 2288 comprising a thin film, polyimide base or substrate.

In some embodiments the 3D structures 2264, or the 3D structures of any of the other multielectrode arrays described herein, can have a tapered, spike or shank-shaped 3D structure. An exemplary 3D structure for the 3D electrodes of any of the multielectrode arrays described herein, having a spike or mosquito-proboscis-like shape are shown in FIGS. 30A and 30B. The 3D electrode structure 2300 shown in the perspective views of FIGS. 30A and 30B can comprise a base 2302, an intermediate shaft portion 2304, and a tip or tip portion 2306. The tip portion 2306 can comprise a sharp tip 2308 that tapers from a sloped base 2310 extending from an end of the shaft portion 2304. The tip portion 2306 can be configured to reduce an insertion force into a tissue (e.g., electrodes having the 3D electrode structure 2300 can be more easily inserted into the tissue, such as the dura, relative to spike or other 3D structures that do not have the rolled, graduated sharp tip sharp of the tip portion). In some examples, the sloped base 2310 can serve as a recording surface of the 3D electrode formed from the 3D electrode structure 2300.

In some examples, the 3D electrode structure 2300 can also include a barb 2312 (or tapered spike or extension) that extends outward from the shaft portion 2304, proximate to the base 2302 (or closer to the base 2302 than to the tip portion 2306). For example, as shown in FIGS. 30A and 30B, the barb 2312 can extend outward at an angle that angles toward the base 2302. The barb 2312 can be configured to anchor the electrode in a tissue (e.g., the dura) when a 3D electrode comprising the 3D electrode structure 2300 is implanted in the tissue of a subject, thereby increasing retention of a 3D electrode or 3D multielectrode comprising electrodes with the 3D electrode structure 2300.

In some examples, the 3D electrode structure 2300 can include a plurality of small barbs (similar to barb 2312) that cover an entirety or a larger portion of the shaft portion 2304 (e.g., like a shark skin or barbs of the jumping cholla).

In some examples, the base 2302 of the 3D electrode structure 2300 can be wider than the sloped base 2310 of the tip portion 2306. In some instances, the base 2302 can have a width or diameter of approximately 40 µm, or in a range of 40-50 µm. Further, in some instances, the sloped base 2310 can have a width or diameter of approximately 20 µm, or in a range of 20-30 µm. Additionally, in some examples, the 3D electrode structure 2300 can have a height (measured from base 2302 to tip 2308) in a range of 300-400 µm. In some examples, the 3D electrode structure 2300 having a shorter height, such as 150 µm, and can still penetrate the dura, due to the shape of the tip portion 2306 described above.

The 3D electrode structure 2300 can comprise a photopolymer coated in metal, thereby forming the 3D electrodes of the multielectrode array 2400 shown in FIG. 31. In some examples, the 3D electrode structures 2300 can be further covered in an insulating layer (e.g., Parylene C or a-SiC), except for the tip portion 2306 (or the tip 2308 of the tip portion 2306).

The 3D multielectrode array 2400 of FIG. 31 can comprise a plurality of 3D electrodes 2402, which in some examples can have the 3D electrode structure 2300 shown in FIGS. 30A and 30B. The 3D multielectrode array 2400 can comprise a thin film (e.g., polyimide) substrate 2404 with each of the 3D electrodes 2402 disposed on the substrate and electrically isolated from adjacent 3D electrodes 2402. Further, each 3D electrode 2402 can be electrically connected (e.g., via an electrical trace) to an electrical connector 2406 (e.g., an Omnetics connector).

Thus, as one example, the 3D multielectrode array 2400 of FIG. 31 can be used as a neural implant configured to be implanted in the brain or spinal cord, wherein the 3D electrodes 2402 are configured to penetrate the dura for single unit recordings.

In some embodiments, the methods described herein for fabricating 3D electronic devices, such as 3D electrode arrays, by selectively metallizing 3D printed structures using photolithography techniques integrated with 3D printing, can be applied to 2D photolithography-based device platforms to create flexible 3D multielectrode arrays that comprise an array of 3D electrodes (e.g., metallized 3D printed structures) on an existing array platform. For example, 3D structures can be 3D printed onto an existing device platform (e.g., a CMOS circuit platform) and then selectively metallized to electrically connect the resulting 3D electrodes to the electronics of the existing device platform.

The 3D electrodes described herein can also be incorporated with (e.g., via 3D printing onto) flexible polymer substrates, such as polyimide substrates. For example, by utilizing flexible substrates, the resulting devices comprising the 3D electrodes can flex and conform to as surface of the brain, thereby reducing distortion and degradation to the tissue that can be associate with more rigid substrate devices.

In this way, 3D electronic devices comprising 3D printed and metallized 3D structures (forming one or more 3D electronic components of the deice) can be formed by integrating 3D printing and photolithography techniques. In some embodiments, 3D structures can be printed onto a prepared substrate using a 3D printer and then selectively metallized such that they are electrically connected to the underlying electrical contacts (or metal traces) of the substrate using photolithography methods. The integration of 3D printing and photolithography allows the formation of 3D electronic devices on the micron scale that can have 3D electronic components (e.g., electrodes) with a high aspect ratio (e.g., greater than ten to one). Further, in some embodiments, 3D printing the 3D structures of the 3D electronic devices, using the high resolution printing methods described herein, can allow for specific geometric features, such as pores, tapered shapes, and relatively small spacing between adjacent 3D electrodes (resulting in a densely packed array) that make the resulting 3D electronic devices suitable for a variety of complex applications. Further, 3D printing the 3D structures for the 3D electronic devices allows for easy and quick device customization based on a desired application. Additionally, the methods described herein can allow the 3D electronic devices to be created on a thin-film flexible substrate (e.g., a flexible polymer, such as polyimide), thereby offering increased flexibility for implantation in a tissue.

In particular, when the 3D electronic device is a 3D multielectrode array or a device including one or more 3D electrodes disposed on a flexible substrate, the device can be advantageous for implantation within the body for neural stimulation and/or recording applications. The specific 3D geometries of the 3D electrodes, including their higher aspect ratio, can allow for better integration with native tissue at the target implantation site, a reduction in scar tissue formation, and an ability to deliver a greater amount of electrical potential, thereby increasing an effectiveness of the devices and enabling the devices to be implanted for longer period of times.

General Considerations

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Features, integers, characteristics, compounds, chemical moieties, or groups described in conjunction with a particular aspect, embodiment or example of the disclosure are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The disclosure is not restricted to the details of any foregoing embodiments. The disclosure extends to any novel one, or any novel combination, of the features disclosed in this specification (including any accompanying claims, abstract, and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language set forth herein. For example, operations described sequentially may in some cases be rearranged or performed concurrently. Moreover, for the sake of simplicity, the attached figures may not show the various ways in which the disclosed methods, systems, and apparatuses can be used in conjunction with other methods, systems, and apparatuses.

As used herein, the terms "a", "an" and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A," "B," "C," "A and B," "A and C," "B and C" or "A, B and C."

As used herein, the term "coupled" generally means physically coupled or linked and does not exclude the presence of intermediate elements between the coupled items absent specific contrary language.

Directions and other relative references (e.g., inner, outer, upper, lower, etc.) may be used to facilitate discussion of the drawings and principles herein, but are not intended to be limiting. For example, certain terms may be used such as "inside," "outside,", "top," "down," "interior," "exterior," and the like. Such terms are used, where applicable, to provide some clarity of description when dealing with relative relationships, particularly with respect to the illustrated embodiments. Such terms are not, however, intended to imply absolute relationships, positions, and/or orientations. For example, with respect to an object, an "upper" part can become a "lower" part simply by turning the object over. Nevertheless, it is still the same part and the object remains the same. As used herein, "and/or" means "and" or "or," as well as "and" and In view of the many possible embodiments to which the principles of the disclosed technology may be applied, it should be recognized that the illustrated embodiments are only preferred examples of the disclosed technology and should not be taken as limiting the scope of the claimed subject matter. Rather, the scope of the claimed subject matter is defined by the following claims and their equivalents.

We claim:

1. A multielectrode array comprising:
   a flexible substrate;
   a plurality of photopatterned electrical traces spaced apart and insulated from one another on the substrate; and
   a plurality of 3D printed electrodes, each 3D printed electrode comprising a photopolymer coated in metal and having a 3D structure that extends outward from the substrate, wherein each 3D printed electrode is electrically connected to a corresponding electrical trace of the plurality of photopatterned electrical traces, wherein the 3D structure comprises a base disposed on the substrate and a shaft portion that extends from the base and narrows to a tip portion of the 3D structure, and wherein the base has a width or diameter in a range of 20-50 μm.

2. The multielectrode array of claim 1, wherein the 3D structure has a conical shape with the tip portion being narrower than the base.

3. The multielectrode array of claim 1, wherein the 3D structure has an aspect ratio of at least 3:1, and wherein the 3D structure has a height in a range of 150-400 μm.

4. The multielectrode array of claim 1, wherein the tip portion comprises a sharp tip that tapers to a point from a sloped base, wherein the sloped base is disposed at an end of the shaft portion and slopes from the end of the shaft portion to the sharp tip, and wherein the 3D structure has a height, measured from the base to the sharp tip, in a range of 300-400 µm.

5. The multielectrode array of claim 1, wherein the multielectrode array is coated with an insulating layer, wherein the tip portion of each 3D electrode comprises exposed metal that is not covered by the insulating layer and a remainder of each 3D electrode, including the shaft portion, is covered by the insulating layer, and wherein the plurality of photopatterned electrical traces is isolated from the environment.

6. The multielectrode array of claim 1, wherein a spacing between adjacent 3D printed electrodes of the plurality of 3D printed electrodes on the substrate is in a range of 30-500 µm.

7. The multielectrode array of claim 1, wherein each 3D printed electrode has an aspect ratio of at least 1:1, and wherein the flexible substrate comprises polyimide.

8. The multielectrode array of claim 1, wherein each 3D electrode is configured to penetrate the dura of the brain.

9. The multielectrode of claim 8, wherein the 3D structure further comprises a barb that extends outward from the shaft portion, proximate to the base, wherein the barb is configured to anchor the 3D electrode in the dura.

10. The multielectrode of claim 1, wherein the multielectrode array is a neural implant configured to be implanted in the brain or spinal cord.

11. The multielectrode array of claim 1, wherein the base has a width or diameter in a range of 40-50 µm.

12. A multielectrode array comprising:
a flexible substrate;
a plurality of photopatterned electrical traces spaced apart and insulated from one another on the substrate; and
a plurality of 3D printed electrodes, each 3D printed electrode comprising a photopolymer coated in metal and having a 3D structure that extends outward from the substrate, wherein each 3D printed electrode is electrically connected to a corresponding electrical trace of the plurality of photopatterned electrical traces, wherein the 3D structure of each 3D printed electrode comprises a plurality of pores.

13. A multielectrode array comprising:
a substrate;
a plurality of photopatterned electrical traces spaced apart and insulated from one another on the substrate, and isolated from the environment; and
a plurality of 3D electrodes, each 3D electrode comprising a photopolymer coated in metal and having a 3D structure that extends outward from the substrate and has an aspect ratio of at least 5:1, wherein each 3D electrode is electrically connected to a corresponding electrical trace of the plurality of photopatterned electrical traces, wherein the 3D structure comprises a base disposed on the substrate and a shaft portion that extends from the base and narrows to a tip portion of the 3D structure, wherein the multielectrode array is coated with an insulating layer, and wherein only the tip portion of each 3D electrode comprises exposed metal that is not covered by the insulating layer and a remainder of each 3D electrode is covered by the insulating layer.

14. The multielectrode array of claim 13, wherein the base has a width or diameter in a range of 20-50 µm.

15. The multielectrode array of claim 13, wherein a height of the 3D structure, measured from the base to a tip of the 3D structure, is in a range of 150-400 µm.

16. The multielectrode array of claim 13, wherein the substrate is a flexible substrate.

17. The multielectrode array of claim 13, wherein a spacing between adjacent 3D electrodes of the plurality of 3D electrodes on the substrate is in a range of 30-500 µm.

18. The multielectrode array of claim 13, wherein the base has a width or diameter of 40 µm, wherein a tip of the tip portion is 20 µm, and wherein a height of the 3D structure, measured from the base to a tip of the 3D structure, is in a range of 300-400 µm.

19. The multielectrode array of claim 13, wherein the base has a width or diameter of 20 µm, and wherein a height of the 3D structure, measured from the base to a tip of the 3D structure, is in a range of 300-400 µm.

20. The multielectrode array of claim 13, wherein each 3D electrode is configured to penetrate the dura of the brain.

* * * * *